(12) United States Patent
Millet

(10) Patent No.: US 12,186,297 B2
(45) Date of Patent: Jan. 7, 2025

(54) COMPOSITIONS AND METHODS FOR INCREASING LEAN-TO-FAT MASS RATIO

(71) Applicant: AXCESS GLOBAL SCIENCES, LLC, Salt Lake City, UT (US)

(72) Inventor: Gary Millet, Salt Lake City, UT (US)

(73) Assignee: AXCESS GLOBAL SCIENCES, LLC, Salt Lake City, UT (US)

( * ) Notice: Subject to any disclaimer, the term of this patent is extended or adjusted under 35 U.S.C. 154(b) by 127 days.

(21) Appl. No.: 17/394,649

(22) Filed: Aug. 5, 2021

(65) Prior Publication Data

US 2022/0062216 A1    Mar. 3, 2022

Related U.S. Application Data

(60) Provisional application No. 63/070,532, filed on Aug. 26, 2020.

(51) Int. Cl.
| | | |
|---|---|---|
| A61K 31/22 | (2006.01) | |
| A61K 31/12 | (2006.01) | |
| A61K 31/19 | (2006.01) | |

(52) U.S. Cl.
CPC ............... *A61K 31/22* (2013.01); *A61K 31/12* (2013.01); *A61K 31/19* (2013.01)

(58) Field of Classification Search
CPC ......... A61K 31/12; A61K 31/19; A61K 31/22
See application file for complete search history.

(56) References Cited

U.S. PATENT DOCUMENTS

| | | | |
|---|---|---|---|
| 2,238,149 | A | 4/1941 | Aeckerle |
| 2,976,073 | A | 3/1961 | Russell et al. |
| 4,139,761 | A | 2/1979 | Obrowski |
| 4,224,503 | A | 9/1980 | Gijzel et al. |
| 4,292,499 | A | 9/1981 | Kleinschmidt et al. |
| 4,627,808 | A | 12/1986 | Hughes |
| 4,771,074 | A | 9/1988 | Lammerant et al. |
| 4,969,393 | A | 11/1990 | Mahlich et al. |
| 4,997,976 | A | 3/1991 | Brunengraber et al. |
| 5,093,044 | A | 3/1992 | Wretlind et al. |
| 5,100,677 | A | 3/1992 | Veech |
| 5,116,868 | A | 5/1992 | Chen et al. |
| 5,288,512 | A | 2/1994 | Seiden |
| 5,292,774 | A | 3/1994 | Hiraide et al. |
| 5,654,266 | A | 8/1997 | Chen et al. |
| 5,700,670 | A | 12/1997 | Yamagishi et al. |
| 6,207,856 | B1 | 3/2001 | Veech |
| 6,217,915 | B1 | 4/2001 | Luchansky et al. |
| 6,232,345 | B1 | 5/2001 | Hiraide et al. |
| 6,316,038 | B1 | 11/2001 | Veech |
| 6,323,237 | B1 | 11/2001 | Veech |
| 6,380,244 | B2 | 4/2002 | Martin et al. |
| 6,613,356 | B1 | 9/2003 | Vlahakos |
| 6,706,756 | B1 | 3/2004 | Fitzpatrick et al. |
| 6,835,750 | B1 | 12/2004 | Henderson |
| 7,351,736 | B2 | 4/2008 | Veech |
| 7,807,718 | B2 | 10/2010 | Hashim et al. |
| 7,891,287 | B2 | 2/2011 | Miller |
| 8,101,653 | B2 | 1/2012 | Veech |
| 8,124,589 | B2 | 2/2012 | Henderson |
| 8,344,896 | B2 | 1/2013 | Ozanne |
| 8,426,468 | B2 | 4/2013 | Henderson |
| 8,642,654 | B2 | 2/2014 | Clarke et al. |
| 8,748,400 | B2 | 6/2014 | Henderson |
| 9,138,420 | B2 | 9/2015 | D'Agostino et al. |
| 9,211,275 | B2 | 12/2015 | Clarke et al. |
| 9,435,566 | B2 | 9/2016 | Hill et al. |
| 9,675,577 | B2 | 6/2017 | D'Agostino et al. |
| 9,717,767 | B2 | 8/2017 | Carpenter et al. |
| 9,795,580 | B2 | 10/2017 | Weeber et al. |
| 9,808,481 | B2 | 11/2017 | Ritter et al. |
| 9,925,164 | B1 | 3/2018 | Hashim |
| 9,957,246 | B2 | 5/2018 | Stinchcomb et al. |
| 10,022,409 | B2 | 7/2018 | Carpenter et al. |
| 10,051,880 | B2 | 8/2018 | Clarke et al. |
| 10,088,197 | B2 | 10/2018 | Hamagami et al. |
| 10,245,242 | B1 | 4/2019 | Millet |

(Continued)

FOREIGN PATENT DOCUMENTS

| | | |
|---|---|---|
| CA | 2990927 A1 | 7/2018 |
| CN | 86108978 A | 11/1987 |

(Continued)

OTHER PUBLICATIONS

Sorensen et al. ("Simultaneous determination of ≠-hydroxybutyrate and β-hydroxy-β-methylbutyrate in human whole blood using hydrophilic interaction liquid chromatography electrospray tandem mass spectrometry", Clinical Biochemistry, 2013, vol. 46, pp. 1877-1883) (Year: 2013).*

A New Toy Measuring Blood Ketones. Diet Doctor, Aug. 21, 2012. Downloaded Apr. 1, 2015. http://www.dietdoctor.com/a-new-toy-measuring-blood-ketoones.

Acetoacetate, Acetone, and Dibenzylamine (A Contaminant in L-(+)-Beta-Hydroxybutyrate) Exhibit Direct Anticonvulsant Actions in Vivo, Epilepsia, Raven Press Ltd, New York, US, vol. 43, No. 4, Apr. 1, 2002 (Apr. 1, 2002), pp. 358-361.

Amazon, "Perfect Keto Perform Pre Workout Powder—Burn Fat for Fuel Energy Supplement Drink Mix for Men and Women—Keto Friendly with Ketone Salts, BCAA, Nitric Oxide & MCT", Sep. 25, 2017 entire document especially p. 1 Retrieved from https://www.amazon.com/Perfect-Keto-Perform-PreworkoutSupplement/dp/B0751379Q9/ref=sr_1_9?dchild=1&keywords=ketone+pre+workout&qid=1597938465&sr=8-9.

(Continued)

*Primary Examiner* — James D. Anderson
(74) *Attorney, Agent, or Firm* — Workman Nydegger

(57) ABSTRACT

Disclosed herein are "ketone body-HMB" or "KB-HMB" compositions including a combination of: (1) hydroxymethyl butyrate; (2) a ketone body component such as beta-hydroxybutyrate (BHB) and/or acetoacetate; and (3) optionally a dietetically or pharmaceutically acceptable carrier. Also disclosed herein are methods of using such compositions for producing desired physiological effects, such as fat loss, in a mammal. The compositions beneficially enhance fat loss through ketosis while also reducing or eliminating muscle wasting and/or promoting muscle formation.

20 Claims, 7 Drawing Sheets

(56) References Cited

U.S. PATENT DOCUMENTS

| | | |
|---|---|---|
| 10,245,243 B1 | 4/2019 | Millet |
| 10,292,592 B2 | 5/2019 | Marshall et al. |
| 10,292,952 B2 | 5/2019 | Millet |
| 10,407,331 B2 | 9/2019 | Kamito et al. |
| 10,512,615 B1 | 12/2019 | Millet |
| 10,588,876 B2 | 3/2020 | Millet |
| 10,588,877 B2 | 3/2020 | Arnold |
| 10,596,128 B2 | 3/2020 | Millet |
| 10,596,129 B2 | 3/2020 | Millet |
| 10,596,130 B2 | 3/2020 | Millet |
| 10,596,131 B2 | 3/2020 | Millet |
| 10,660,958 B2 | 5/2020 | Clarke |
| 10,736,861 B2 | 8/2020 | Millet |
| 10,792,269 B2 | 10/2020 | Hashim |
| 10,925,843 B2 | 2/2021 | Millet |
| 10,973,786 B2 | 4/2021 | Millet |
| 10,980,764 B1 | 4/2021 | D'Agostino et al. |
| 10,980,772 B2 | 4/2021 | Millet |
| 11,020,362 B2 | 6/2021 | Millet |
| 11,033,553 B2 | 6/2021 | Millet |
| 11,103,470 B2 | 8/2021 | Millet |
| 11,129,802 B2 | 9/2021 | Millet |
| 11,173,138 B2 | 11/2021 | Lowery et al. |
| 11,185,518 B2 | 11/2021 | Millet |
| 11,202,769 B2 | 12/2021 | Millet |
| 11,241,403 B2 | 2/2022 | Millet |
| 11,690,817 B2 | 7/2023 | Millet |
| 11,793,778 B2 | 10/2023 | Millet |
| 11,806,324 B2 | 11/2023 | Millet |
| 11,944,598 B2 | 4/2024 | Millet |
| 11,950,616 B2 | 4/2024 | Millet |
| 2001/0014696 A1 | 8/2001 | Veech |
| 2001/0018866 A1 | 9/2001 | Fischer |
| 2001/0041736 A1 | 11/2001 | Veech |
| 2002/0013339 A1 | 1/2002 | Martin et al. |
| 2003/0022937 A1 | 1/2003 | Veech |
| 2004/0138293 A1 | 7/2004 | Werner et al. |
| 2004/0266872 A1 | 12/2004 | Veech |
| 2005/0129783 A1 | 6/2005 | McCleary et al. |
| 2005/0169968 A1 | 8/2005 | Elmaleh et al. |
| 2006/0165777 A1 | 7/2006 | Solomon et al. |
| 2006/0275253 A1 | 12/2006 | Ushida et al. |
| 2007/0029913 A1 | 2/2007 | Chen |
| 2007/0135376 A1 | 6/2007 | Henderson |
| 2007/0179197 A1 | 8/2007 | Henderson |
| 2008/0058416 A1 | 3/2008 | Greenwood et al. |
| 2008/0287372 A1 | 11/2008 | Henderson |
| 2009/0131475 A1 | 5/2009 | Uesugi et al. |
| 2009/0253781 A1 | 10/2009 | Veech |
| 2010/0041751 A1 | 2/2010 | Henderson |
| 2010/0056631 A1 | 3/2010 | Hisamura et al. |
| 2010/0197758 A1 | 8/2010 | Andrews et al. |
| 2010/0210726 A1 | 8/2010 | Kuriyama |
| 2010/0298294 A1 | 11/2010 | Clarke et al. |
| 2011/0237666 A1 | 9/2011 | Clarke et al. |
| 2011/0287114 A1 | 11/2011 | Johnson |
| 2012/0053240 A1 | 3/2012 | Rathmacher et al. |
| 2012/0071548 A1 | 3/2012 | Veech |
| 2012/0171165 A1 | 7/2012 | Buck et al. |
| 2012/0202891 A1 | 8/2012 | Stinchcomb et al. |
| 2013/0079406 A1 | 3/2013 | Veech |
| 2013/0337116 A1 | 12/2013 | Petralia |
| 2014/0256808 A1 | 9/2014 | Henderson |
| 2014/0329893 A1 | 11/2014 | Veech |
| 2014/0350105 A1* | 11/2014 | D'Agostino .......... A61K 31/19 514/547 |
| 2014/0352728 A1 | 12/2014 | Svensson |
| 2015/0065571 A1 | 3/2015 | Clarke et al. |
| 2015/0132280 A1 | 5/2015 | Lopez et al. |
| 2015/0144074 A1 | 5/2015 | Fujimoto et al. |
| 2015/0320809 A1 | 11/2015 | Carpenter et al. |
| 2015/0363750 A1 | 12/2015 | Svensson et al. |
| 2016/0193173 A1 | 7/2016 | Clarke et al. |
| 2016/0256411 A1 | 9/2016 | Aung-Din |
| 2016/0263071 A1 | 9/2016 | Borges et al. |
| 2017/0020844 A1 | 1/2017 | Galinski |
| 2017/0029650 A1 | 2/2017 | Veling et al. |
| 2017/0172969 A1 | 6/2017 | D'Agostino et al. |
| 2017/0258745 A1 | 9/2017 | Millet |
| 2017/0266148 A1 | 9/2017 | D'Agostino et al. |
| 2017/0290792 A1 | 10/2017 | Cavaleri |
| 2017/0296501 A1 | 10/2017 | Lowery et al. |
| 2017/0298339 A1 | 10/2017 | Hanson et al. |
| 2017/0304564 A1 | 10/2017 | Dehaan et al. |
| 2018/0021274 A1 | 1/2018 | Arnold |
| 2018/0021281 A1 | 1/2018 | Berger |
| 2018/0055797 A1 | 3/2018 | Llosa et al. |
| 2018/0057846 A1 | 3/2018 | Llosa et al. |
| 2018/0195096 A1 | 7/2018 | Veech et al. |
| 2018/0214399 A1 | 8/2018 | Spector et al. |
| 2018/0238586 A1 | 8/2018 | Sugatani et al. |
| 2019/0099394 A1 | 4/2019 | Ari et al. |
| 2019/0151267 A1 | 5/2019 | Millet |
| 2019/0167613 A1 | 6/2019 | Millet |
| 2019/0167614 A1 | 6/2019 | Millet |
| 2019/0177673 A1 | 6/2019 | Llosa et al. |
| 2019/0183220 A1 | 6/2019 | Takada |
| 2019/0183820 A1 | 6/2019 | Millet |
| 2019/0183821 A1 | 6/2019 | Millet |
| 2019/0191755 A1 | 6/2019 | Garvey et al. |
| 2019/0209501 A1 | 7/2019 | Tinsley et al. |
| 2019/0262293 A1 | 8/2019 | Millet |
| 2019/0313682 A1 | 10/2019 | Nagel |
| 2019/0321309 A1 | 10/2019 | Millet |
| 2020/0078973 A1 | 3/2020 | Valeze et al. |
| 2020/0140371 A1 | 5/2020 | Verdin et al. |
| 2020/0253909 A1 | 8/2020 | Millet |
| 2020/0268701 A1 | 8/2020 | D'Agostino et al. |
| 2021/0095867 A1 | 4/2021 | Gururaja et al. |
| 2021/0106168 A1 | 4/2021 | Cingolani et al. |
| 2021/0205241 A1 | 7/2021 | Millet |
| 2024/0024265 A1 | 1/2024 | Millet |
| 2024/0197668 A1 | 6/2024 | Millet |

FOREIGN PATENT DOCUMENTS

| | | |
|---|---|---|
| CN | 1256629 A | 6/2000 |
| CN | 1347319 A | 5/2002 |
| CN | 1972698 A | 5/2007 |
| CN | 101674730 A | 3/2010 |
| CN | 101678043 A | 3/2010 |
| CN | 101969769 A | 2/2011 |
| CN | 102164884 A | 8/2011 |
| CN | 104224823 A | 12/2014 |
| CN | 105050594 A | 11/2015 |
| CN | 106038532 A | 10/2016 |
| CN | 106459646 A | 2/2017 |
| CN | 106858066 A | 6/2017 |
| CN | 108253621 A | 7/2018 |
| CN | 109480284 A | 3/2019 |
| DE | 102017210992 A1 | 1/2019 |
| EP | 0008700 A1 | 3/1980 |
| EP | 1112711 A1 | 7/2001 |
| EP | 1178748 A1 | 2/2002 |
| EP | 1827412 A1 | 9/2007 |
| EP | 1915144 A2 | 4/2008 |
| EP | 2283834 A2 | 2/2011 |
| EP | 2976073 A1 | 1/2016 |
| EP | 3094321 A1 | 11/2016 |
| EP | 3366173 A2 | 8/2018 |
| EP | 3446045 A1 | 2/2019 |
| FR | 2997302 A1 | 5/2014 |
| GB | 2391493 A | 2/2004 |
| ID | 201701176 | 2/2017 |
| JP | 11-060434 A | 3/1999 |
| JP | 2002-521330 A | 7/2002 |
| JP | 2004-035417 A | 2/2004 |
| JP | 2015-042644 A | 3/2015 |
| JP | 2015-514104 A | 5/2015 |
| JP | 2015-102323 A | 6/2015 |
| JP | 2016-514725 A | 5/2016 |
| JP | 2016-121128 A | 7/2016 |
| JP | 2017-046688 A | 3/2017 |
| JP | 2020-502652 A | 1/2020 |

(56) References Cited

FOREIGN PATENT DOCUMENTS

| | | |
|---|---|---|
| JP | 2020-527583 A | 9/2020 |
| JP | 2021-504476 A | 2/2021 |
| JP | 2021-506294 A | 2/2021 |
| RU | 2345546 C2 | 2/2009 |
| WO | 87/03808 A1 | 7/1987 |
| WO | 98/41200 A1 | 9/1998 |
| WO | 00/69315 A1 | 11/2000 |
| WO | 03/70823 A2 | 8/2003 |
| WO | 2005/107724 A1 | 11/2005 |
| WO | 2006/061624 A1 | 6/2006 |
| WO | 2007/115282 A2 | 10/2007 |
| WO | 2008/005818 A1 | 1/2008 |
| WO | 2008/021394 A2 | 2/2008 |
| WO | 2008/024408 A2 | 2/2008 |
| WO | 2009/089144 A1 | 7/2009 |
| WO | 2010/021766 A1 | 2/2010 |
| WO | 2011/101171 A1 | 8/2011 |
| WO | 2012/019295 A1 | 2/2012 |
| WO | 2013/057506 A1 | 4/2013 |
| WO | 2013/150153 A1 | 10/2013 |
| WO | 2014/153416 A1 | 9/2014 |
| WO | 2015/071811 A1 | 5/2015 |
| WO | 2015/156865 A1 | 10/2015 |
| WO | 2016/123229 A1 | 8/2016 |
| WO | 2016/149687 A1 | 9/2016 |
| WO | 2017/156446 A1 | 9/2017 |
| WO | 2017/165443 A1 | 9/2017 |
| WO | 2017/165445 A1 | 9/2017 |
| WO | 2017/182664 A1 | 10/2017 |
| WO | 2017/208217 A2 | 12/2017 |
| WO | 2018/055388 A1 | 3/2018 |
| WO | 2018/089863 A1 | 5/2018 |
| WO | 2018/114309 A1 | 6/2018 |
| WO | 2018/175879 A1 | 9/2018 |
| WO | 2018/187324 A1 | 10/2018 |
| WO | 2018/187852 A1 | 10/2018 |
| WO | 2019/018683 A1 | 1/2019 |
| WO | 2019/108683 A1 | 6/2019 |
| WO | 2019/204148 A1 | 10/2019 |
| WO | 2019/237152 A1 | 12/2019 |
| WO | 2020/041871 A1 | 3/2020 |

OTHER PUBLICATIONS

Arendash et al. "Caffeine and Coffee as Therapeutics Against Alzheimer's Disease", Journal of Alzheimer's Disease 20, 2010, S117-S126.
Bastin et al., "Salt Slection and Optimisation Procedures for Pharmaceutical New Chemical Entities", American Chemical Society and The Royal Society of Chemistry, vol. 4, No. 5, 2000, pp. 427-435.
Blazquez et al. Journal of Neurochemistry, 1999, vol. 72 No. 4, pp. 1759-1768. (Year: 1999).
Clarke, et al., Kinetics, safety and tolerability of (R)-3-hydroxybutyl (R)-3-hydroxybutyrate in healthy adult subjects. Regul Toxicol Pharmacol. Aug. 2012; 63(3):401-8.
Craciun, S. et al. Microbial conversion of choline to trimethylamine requires a glycyl radical enzyme, 2012, PNAS, 109(52): 21307-21312 (Year: 2012).
Cresci, G. et al., Lactobacillus GG and Tributyrin Supplementation Reduce Antibiotic-Induced Intestinal Injury, 2013, Journal of Parenteral and Enteral Nutrition, 37(6), 1-20 (Year: 2013).
Dietary Guidelines Recommendations at https://health.gov/our-work/food-nutrition/2015-2020-dietary-guidelines/guidelines/ appendix-7/ (2010) (retrieved from the internet Oct. 20, 2020) (Year: 2010).
Dolson, Laura. How to Test Your Blood for Ketones. Downloaded Apr. 1, 2015. http://lowcarbdiets.about.eom/od/KetogenicDiets/a/How-to-Test-Blood-For-Ketones.htm.
Extended European Search Report issued in PCT/US2017021886 dated Oct. 17, 2019.
First Examination Report for New Zealand Patent Application No. 711433 issued by the New Zealand Intellectual Property Office dated Mar. 10, 2016.

First Office Action issued by the Chinese State Intellectual Property Office on Nov. 4, 2016 for corresponding Chinese Patent Application No. 201480016818.0.
Haces M L et al: "Antioxidant capacity contributes to protection of ketone bodies against oxidative damage induced during hypoglycemic conditions", Experimental Neurology, Elsevier, Amsterdam, NL, vol. 211, No. 1, May 1, 2008 (May 1, 2008), pp. 85-96.
Hashim, Sami A., et al., "Ketone body therapy: from the ketogenic diet to the oral administration of ketone ester", Journal of Lipid Research, vol. 55, 2014.
Haywood A, Glass BD. Pharmaceutical excipients—where do we begin? Australian Prescriber. 2011; 34: 112-114.
Henderson, Samuel T. "Ketone Bodies as a Therapeutic for Alzheimer's Disease." Neurotherapeutics. Jul. 2008; 5(3):470-80.
Holtzman et al., "Role of adenosine receptors in caffeine tolerance", J. Pharmacol. Exp. Ther., 1991 ; 256(1 ):62-68.
Ichim, T. et al., Experimental support for the effects of a probiotic/digestive enzyme supplement on serum cholesterol concentrations and the intestinal microbiome, 2016, Journal of Translational Medicine, 14(184), 1-9 (Year: 2016).
International Preliminary Report on Patentability received for PCT Patent Application No. PCT/US2020/016952, mailed on Aug. 26, 2021, 7 pages.
International Preliminary Report on Patentability received for PCT Patent Application No. PCT/US2019/048364, mailed on Mar. 11, 2021, 7 pages.
International Preliminary Report on Patentability received for PCT Patent Application No. PCT/US2020/017552, mailed on Aug. 26, 2021, 7 pages.
International Preliminary Report on Patentability received for PCT Patent Application No. PCT/US2020/017555, mailed on Aug. 26, 2021, 7 pages.
International Preliminary Report on Patentability received for PCT Patent Application No. PCT/US2020/017556, mailed on Aug. 26, 2021, 7 pages.
International Preliminary Report on Patentability received for PCT Patent Application No. PCT/US2020/033159, mailed on Nov. 25, 2021, 6 pages.
International Search Report and Written Opinion issued in PCT/US19/48357 dated Nov. 18, 2019.
International Search Report and Written Opinion issued in PCT/US19/48364 dated Nov. 15, 2019.
International Search Report and Written Opinion issued in PCT/US20/16952 dated Apr. 22, 2020.
International Search Report and Written Opinion issued in PCT/US20/17552 dated May 4, 2020.
International Search Report and Written Opinion issued in PCT/US20/17555 dated May 4, 2020.
International Search Report and Written Opinion issued in PCT/US20/17556 dated May 4, 2020.
International Search Report and Written Opinion received for PCT Patent Application No. PCT/US20/017555, mailed on May 4, 2020, 8 pages.
International Search Report and Written Opinion received for PCT Patent Application No. PCT/US20/37289, mailed or Sep. 30, 2020, 8 pages.
International Search Report and Written Opinion received for PCT Patent Application No. PCT/US2020/033159, mailed on Aug. 12, 2020, 9 pages.
International Search Report and Written Opinion received for PCT Patent Application No. PCT/US21/17078, mailed on Apr. 23, 2021, 9 pages.
International Search Report cited in PCT/US18/62093 dated Feb. 1, 2019.
International Search Report cited in PCT/US19/27214 dated Jun. 25, 2019.
It Really is in Your Blood: Glucose to Ketone Ratios. Greymadder, Sep. 15, 2014. Downloaded Apr. 1, 2015. http://greymadder.net/2014/09/15/it-really-is-in-your-blood-glucose-to-ketone-ratios/.
James, "Optical Purity and Enantiomeric Excess" at https://www.masterorganicchemistry.com/2017/02/24/optical-purity-and-enantiomeric-excess/. (Retrieved from the internet Nov. 6, 2018) (Year: 2018).

(56) References Cited

OTHER PUBLICATIONS

Karppanen et al, J. Human Hypertension (2005), vol. 19, pp. S10-S19. (Year: 2005).
Kesl, et al., "Effects of exogenous ketone supplementation on blood ketone, glucose, triglyceride, and lipoprotein levels in Spraque-Dawley rats", Nutrition & Metabolism (2016).
Kirsch, JR et al. "Butanediol Induced Ketosis Increases Tolerance to Hypoxia in the Mouse." Stroke. 1980. vol. 11, No. 5, pp. 506-513.
Kossoff, Eric H. et al. "Optimal Clinical Management of Children Receiving the Ketogenic Diet: Recommendations of the International Ketogenic Diet Study Group." Epilepsia, Feb. 2009; 50(2):304-17. Epub Sep. 23, 2008.
European Search Report received for EP Patent Application No. 20805593.9, mailed on Dec. 16, 2022, 9 pages.
Maguire et al., "Gut dysbiosis, leaky gut, and intestinal epithelial proliferation in neurological disorders: towards the development of a new therapeutic using amino acids, prebiotics, probiotics, and postbiotics", Rev Neurosci . Jan. 28, 2019, vol. 30, No. 2, pp. 179-201.
Rich A.J., "Ketone Bodies as Substrates," Proceedings of the Nutrition Society (1990), vol. 49, 361-373.
Wu et al., "Medium-Chain Triglycerides in Infant Formulas and Their Relation to Plasma Ketone Body Concentrations," Pediatric Research, vol. 20, No. 4, (1986), pp. 338-341.
Yang Y. et al., Role of Adherent-Invasive *Escherichia coli* in Inflammatory Bowl Disease, Letters in Biotechnology , No. 06, Nov. 30, 2016.
European Search Report received for EP Patent Application No. 20755289.4, mailed on Oct. 11, 2022, 7 pages.
European Search Report received for EP Patent Application No. 20755994.9, mailed on Sep. 21, 2022, 6 pages.
Extended European Search Report received for EP Patent Application No. 20755770.3, mailed on Sep. 1, 2022, 7 pages.
Grootaert, C. Comparison of prebiotic effects of arabinoxylan oligosaccharides and inulin in a simulator of the human intestinal microbial ecosystem, 2009, FEMS Microbiology Ecology, 69: 231-242 (Year: 2009).
Holscher, H. Dietary fiber and prebiotics and the gastrointestinal microbiota, 2017, Gut Microbes, 8(2): 172-184 (Year: 2017).
International Preliminary Report on Patentability received for PCT Patent Application No. PCT/US2021/017078, mailed on Aug. 18, 2022, 7 pages.
International Search Report and Written Opinion received for PCT Patent Application No. PCT/US2021/063559, mailed on Mar. 18, 2022, 9 pages.
John C Newman et al: "beta-Hydroxybutyrate: A Signaling Metabolite", Annual Review of Nutrition, vol. 37, Aug. 21, 2017 (Aug. 21, 2017), pp. 51-76, XP055771586.
Lile et al. Drug Alcohol Depend. 2012, 122 (1-2), 61-69.
National Center for Biotechnology Information. PubChem Compound Summary for CID 441, 3-Hydroxybutyric acid, https://pubchem.ncbi.nlm.nih.gov/compound/3-Hydroxybutyric-acid. (Year: 2005).
Parker, Steve, "Ketogenic Mediterraanean Diet: Version 2.3," Nov. 23, 2010, pp. 1-3. (Year: 2010).
Sanchez, J. I. et al. Arabinoxylan-oligosaccharides (AXOS) affect the protein/carbohydrate fermentation balance and microbial population dynamics of the Simulator of Human Intestinal Microbial Ecosystem, 2009, Microbial Biotechnology, 2(1): 101-113 (Year: 2009).
Slavin, J. Fiber and Prebiotics: Mechanisms and Health Benefits, 2013, Nutrients, 5: 1417-1425 (Year: 2013).
The Medical Republic, 2018, Sustained Release Sodium Butyrate Supplement Now Available to Support Management of GI Disorders, https://medicalrepublic.com.au/sustained-release-sodium-butyrate-supplement-now-available-support-management-gi-disorders/15791; newly cited (Year: 2018).
Walton, G. et al. A randomised, double-blind, placebo controlled cross-over study to determine the gastrointestinal effects of consumption of arabinoxylan-oligosaccharides enriched bread in healthy volunteers, 2012, Nutrition Journal, 11(36): 1-11 (Year: 2012).
Zaleski, A. et al., Butyric acid in irritable bowel syndrome, 2013, Prz Gastroenterol, 8(6), 350-353 (Year: 2013).
Extended European Search Report received for EP Patent Application No. 19788264.0, mailed on Dec. 20, 2021, 11 pages.
International Preliminary Report on Patentability received for PCT Patent Application No. PCT/US20/37289, mailed on Dec. 30, 2021, 6 pages.
International Search Report and Written Opinion received for PCT Patent Application No. PCT/US21/045186, mailed on Nov. 22, 2021, 10 pages.
Kim Do Young et al., "Ketone bodies are protective against oxidative stress in neocortical neurons," Journal of Neurochemistry, vol. 101, Issue 5, Jun. 1, 2007, pp. 1316-1326.
Maalouf Met al., "Ketones inhibit mitochondrial production of reactive oxygen species production following glutamate excitotoxicity by increasing NADH oxidation," Neuroscience, New York, NY, US, vol. 145, Issue 1, Mar. 2, 2007, pp. 256-264.
Maalouf Met al., "The neuroprotective properties of calorie restriction, the ketogenic diet, and ketone bodies," Brain Research Reviews, Elsevier, NL, vol. 59, No. 2, Mar. 1, 2009, pp. 293-315.
Pete J Cox et al., "Acute nutritional ketosis: implications for exercise performance and metabolism," Extreme Physiology & Medicine, vol. 3, Issue 1, Dec. 1, 2014, pp. 1-9.
Krotkiewski, "Value of VLCD Supplementation with Medium Chain Triglycerides", Int J Obes Relat Metab Disord, Sep. 2001, 25(9), pp. 1393-1400.
Malo, M. S. et. al., Intestinal alkaline phosphatase preserves the normal homeostasis of gut microbiota, 2010, Gut, 59, 1476-1484 (Year: 2010).
Murray, Andrew J., et al. "Novel ketone diet enhances physical and cognitive performance", The FASEB Journal, No. Dec. 30, 2016.
Nova Max Plus Glucose and Ketone Testing with One Monitor. Downloaded Apr. 1, 2015. http://www.novacares.com/nova-max-plus/.
Optical Purity and Enantiomeric Excess at https://www.masterorganicchemistry.com/2017/02/24/optical-purity-and-enantiomeric-excess/. (Retrieved from the internet Nov. 6, 2018) (Year: 2018).
Parker, Steve, "Ketogenic Mediterranean Diet: Version 2.3," Nov. 23, 2010, pp. 1-3. (Year: 2010).
PCT International Search Report and Written Opinion issued by the International Searching Authority on Jul. 15, 2014 or International Patent Application No. PCT/US2014/031237.
Precision Xtra vs. NovaMax Plus: Ketone Meter Evaluation. Jimmy Moore's Livin' La Vida Low Garb Blog. Downloaded Apr. 1, 2015. http://livinlavidalowcarb.com/blog/precision-xtra-vs-novamax-plus-ketone-meter-evaluation/15918.
Pubchem, "Acetoacetic acid" Electronic Resource: https://pubchem.ncbi.nim.nih.gov/compound/Acetoacetic-acid, Retrieved on Sep. 3, 2019.
Robson et al. Expert Opin. Drug Saf. (2011), vol. 10, pp. 675-685 (Year: 2011).
Roeder, Lois M., et al. The Effects of Ketone Bodies, Bicarbonate, and Calcium on Hepatic Mitochondrial Ketogenesis. Archives of Biochemistry and Biophysics, vol. 217, No. 2, Sep. pp. 460-467, 1982.
Sajewicz et al. In Journal of Liquid Chromatography & Related Technologies, 33:1047-1057 (2010) (Year: 2010).
Serum Ketones Test. MedlinePlus Medical Encyclopedia. Downloaded Apr. 1, 2015. http://www.nlm.nih.gov/medlineplus/ency/article/003498.htm.
Shigeno et al. In Biosci. Biotech. Biochem., 56(2), 320-323 (1992) (Year: 1992).
Stubbs et al., "On the Metabolism of Exogenous Ketones in Humans", frontiers in Physiology, vol. 8, 2017, 13 pages.
Tanaka, J., et al., "Significance of Blood Ketone Body Ration as an indicator of Hepatic Cellular Energy Status in Jaundiced Rabbits", Gastroenterology, 1979, vol. 76, No. 4, pp. 691-696.
Tisdale, "Reduction of weight loss and tumour size in a cachexia model by a high fat diet", British Journal of Cancer, Jul. 1987, vol. 56, p. 39-43.

(56) References Cited

OTHER PUBLICATIONS

Tsai et al., "Stereoselective effects of 3-hydroxybutyrate on glucose utilization of rat cardiomyocytes" life Sciences 78(2006) pp. 1385-1391.
Vandenberghe et al. In Can. J. Physiol. Pharmacol. 95: 455-458 (2017) (Published at www.nrcresearchpress.com/cjpp on Nov. 25, 2016). (Year: 2016).
Veech, et al., "Ketone Bodies Mimic the Life Span Extending Properties of Caloric Restriction", IUBMB Life Feb. 8, 2017.
Veech, Richard L. "The Therapeutic Implications of Ketone Bodies: The Effects of Ketone Bodies in Pathological Conditions: Ketosis, Ketogenic Diet, Redox States, Insulin Resistance, and Mitochondrial Metabolism." Prostaglandins Leukot Essent Fatty Acids. Mar. 2004;70(3):309-19.
Vorgerd, M. And J. Zange. Treatment of glycogenosys type V (McArdle disease) with creatine and ketogenic diet with clinical scores and with 31P-MRS on working leg muscle. Acta Myologica, 2007; XXVI; pp. 61-63.
Anonymous: "Blue Lemon Ice Advanced Formula", MINTEL, Database accession No. 4315637, 2016, pp. 3.
Anonymous: "Strawberry Pineapple Flavour Pre-Exertion Performance Optimizer", MINTEL, Database accession No. 5661617, 2018, pp. 4.
Budin. N. et al., "Efficient synthesis of the ketone body ester (R)-3-hydroxybutyryl-(R)-3-hydroxybutyrate and its (S, S) enantiomer," Bioorganic Chemistry, vol. 80, Oct. 2018, pp. 560-564.
Huang Dexiang, "Clinical Parenteral nutrition", Jan. 31, 1994, pp. 1-20.
International Preliminary Report on Patentability received for PCT Patent Application No. PCT/US2018/062093, mailed on Jun. 4, 2020, 6 pages.
International Preliminary Report on Patentability received for PCT Patent Application No. PCT/US2021/045186, mailed on Mar. 9, 2023, 7 pages.
International Preliminary Report on Patentability received for PCT Patent Application No. PCT/US2021/050302, mailed on Mar. 2, 2023, 8 pages.
Kaster M.P. et al, "Caffeine acts through neuronal adenosine A2A receptors to prevent mood and memory dysfunction triggered by chronic stress", Proceedings of the National Academy of Sciences, vol. 112, No. 25, Jun. 8, 2015, pp. 7833-7838.
Lonza, Duocap Capsules, Feb. 16, 2018, https://web.archive.org/web/20180216001656/https://www.capsugel.com/consumer-health-nutrition-products/duocap-capsules (Year: 2018).
Luis Villasenor, "Supplements and Ketogenic Diets—Facts and Myths", Retrieved from https://www.ketogains.com/2015/09/supplements-and-ketogenic-diets-facts-and-myths/, Sep. 18, 2015, pp. 15.
Lytra. G. et al., "Distribution and Organoleptic Impact of Ethyl 3-Hydroxybutanoate Enantiomers in Wine," J. Agric. Food Chem, vol. 63, Issue 48, 2015, pp. 10484-10491.
Mangels D.R. et al, "Catechins as Potential Mediators of Cardiovascular Health", Translational Sciences, vol. 37, No. 5, May 1, 2017, pp. 757-763.
Arnold, Instant Ketosis?, (2013), Aug. 4, 2013 (retrieved on Apr. 21, 2017), p. 1-3. Retrieved from the internet; URL: < http://patrickarnoldblog.com/instant-ketosis/. (Year: 2013).
Bala et al. Drug Invention Today. Jun. 1, 2018;10(6), 929-931.
International Preliminary Report on Patentability received for PCT Patent Application No. PCT/US2014/031237, mailed on Oct. 1, 2015, 8 pages.
International Preliminary Report on Patentability received for PCT Patent Application No. PCT/US2017/021886, mailed on Sep. 20, 2018, 9 pages.
International Preliminary Report on Patentability received for PCT Patent Application No. PCT/US2018/062096, mailed on Jul. 2, 2020, 8 pages.
International Preliminary Report on Patentability received for PCT Patent Application No. PCT/US2019/027214, mailed on Oct. 29, 2020, 09 pages.
International Preliminary Report on Patentability received for PCT Patent Application No. PCT/US2019/048357, mailed on Mar. 11, 2021, 08 pages.
International Preliminary Report on Patentability received for PCT Patent Application No. PCT/US2021/063559, mailed on Jul. 6, 2023, 6 pages.
International Search Report and Written Opinion received for PCT Patent Application No. PCT/US2014/031237, mailed on Jul. 15, 2014, 11 pages.
International Search Report and Written Opinion received for PCT Patent Application No. PCT/US2017/021886, mailed on Jun. 1, 2017, 15 pages.
International Search Report and Written Opinion received for PCT Patent Application No. PCT/US2018/062096, mailed on Feb. 11, 2019, 13 pages.
International Search Report and Written Opinion received for PCT Patent Application No. PCT/US2019/027214, mailed on Jun. 25, 2019, 14 pages.
International Search Report and Written Opinion received for PCT Patent Application No. PCT/US2019/048357, mailed on Nov. 18, 2019, 13 pages.
International Search Report and Written Opinion received for PCT Patent Application No. PCT/US2020/016952, mailed on Apr. 22, 2020, 9 pages.
International Search Report and Written Opinion received for PCT Patent Application No. PCT/US2020/017552, mailed on May 4, 2020, 9 pages.
International Search Report and Written Opinion received for PCT Patent Application No. PCT/US2020/017556, mailed on May 4, 2020, 12 pages.
Lang Chaochun, "Healthy fitness and exercise prescription", Nov. 30, 2013, p. 201.
O'Meara, Cyndi, Changing Habits, Ketosis—Can we achieve it in a pill?, https://changinghabits.com.au/ketosis-can-we-achieve-it-in-a-pill/, 12 pages, (Jan. 13, 2017).
Sara, How do you know which product is right for you? How to choose exogenous ketones, https://ketosupplements.co.uk/how-to-choose-exogenous-ketones/, 10 pages, (Sep. 25, 2017).
Short, Jay, Effects of A Ketone/Caffeine Supplement On Cycling and Cognitive Performance, Master's thesis, Ohio State University, 61 pages, (Jan. 1, 2017).
Yang Yue et al., "Research on sarcopenic obesity", Chinese Journal of Modern Medicine, vol. 20, No. 3, Mar. 25, 2018, pp. 98-101.
Yang Zeyi, "Biochemistry of sports nutrition scientific research progress", Mar. 31, 2004, vol. 23, No. 2, pp. 158-165.
Zeng Jing et al., "B-hydroxy-3-methyl—The clinical effects and mechanism", vol. 2, No. 2, Jun. 9, 2015, pp. 57-62.
European Search Report received for EP Patent Application No. 21750261.6, mailed on Feb. 2, 2024, 10 pages.
O'Mailey et al, Appl. Physiol. Nutr. Metab. 42: 1031-1035 (2017) Published at www.NRCRESEARCHPRESS.com/APNM on Jul. 27, 2017.
Office Action received for European Patent Application No. 19788264.0, mailed on Mar. 13, 2024, 5 pages.
Office Action received for European Patent Application No. 20805593.9, mailed on Dec. 22, 2023, 7 pages.
WO2009045481, Pan et al. Published Apr. 9, 2009 Listed in this section as citation type "foreign" does not allow for any appropriate country code for "WO" documents.
European Search Report received for EP Patent Application No. 21862356.9, mailed on Jul. 1, 2024, 10 pages.

* cited by examiner

COMPOSITIONS AND METHODS FOR INCREASING LEAN-TO-FAT MASS RATIO

CROSS-REFERENCE TO RELATED APPLICATIONS

This application claims the benefit of U.S. Provisional Application No. 63/070,532, filed Aug. 26, 2020, which is incorporated by reference in its entirety.

BACKGROUND

Body Mass and Body Shaping

Although many people desire to lose body fat, build muscle, and generally increase their lean-to-fat mass ratio, achieving this outcome is often difficult. The rate of failure is high as evidenced by increasing rates of obesity. For some, this is due to poor nutrition and overeating. For others, it is living a sedentary lifestyle. Even people who exercise hard and try to eat responsibly can find it difficult to improve their lean-to-fat mass ratio.

Most people try to lose weight through dieting and exercise, which generally leads to better health. People sometimes turn to fad diets as a shortcut. The problem is that nutritional standards seem to be ever changing. For decades, people were told to eat a balanced diet from the four food groups. Then, there was the low-fat, high carb craze that arose out of the food pyramid that replaced the four food groups, which is now acknowledged to be a complete failure, leading to higher rates of obesity and diabetes through excess consumption of sugars and high glycemic foods. This was replaced by high fat, low carb diets that forced the body to preferentially burn fat instead of carbs. Though successful for some, it led many to overeat, such as by consuming excessive meat, which caused other health problems. There are now many fad diets, such as paleo, Mediterranean, ketogenic, and others, with mixed results. The problem with most diets and exercise is inconsistency and discouragement.

Others seek to build body mass through intense weight lifting, which is anabolic and simultaneously builds muscle and increases fat, followed by caloric restriction to catabolically reduce the fat without losing too much of the gained muscle mass. This cycle of "bulking" and "cutting" is well-known to bodybuilders and other athletes. The goal is typically to gain more net muscle overall, even though it is taken as a given that fat will increase during the bulking phase and muscle will be lost during the cutting phase. While effective for the highly disciplined, those with certain body types, and younger people, it is a less effective prescription for the average person.

In general, loss of lean muscle mass is often associated with fasting and/or a ketogenic diet. Simply put, it is difficult for the body to build or even preserve muscle while also losing fat. Generally, the body is either in an overall anabolic state where both muscle and fat are gained, or an overall catabolic state where both muscle and fat are reduced.

Ketosis & Ketone Bodies

In periods of fasting, extreme exercise, and/or low carbohydrate consumption, glucose and glycogen stores in the body are rapidly used and can become quickly depleted. Failure to replenish glucose stores as they become depleted causes the body to metabolically shift to the creation of ketone bodies for energy. This metabolic state is called "ketosis".

Ketone bodies can be used by cells of the body as a fuel in addition or instead of glucose to satisfy the body's energy needs, including the brain and heart. During prolonged fasting, for example, blood ketone levels can increase to 2-3 mmol/L or more. It is conventionally understood that when blood ketones rise above 0.5 mmol/L, the heart, brain and peripheral tissues are using ketone bodies (e.g., beta-hydroxybutyrate and acetoacetate) as the primary fuel source. This condition is referred to as ketosis. Between 1.0 mmol/L and 3.0 mmol/L the condition is called "nutritional ketosis."

Upon transitioning into ketosis, or in other words, during ketogenic metabolism in the liver, the body uses dietary and bodily fats as a primary energy source. Consequently, once in ketosis, one can induce loss of body fat by controlling dietary fat intake and maintaining low carbohydrate intake to maintain a ketogenic metabolic state.

While in ketosis, the body is essentially burning fat for its primary fuel. The body initially cleaves fats into fatty acids and glycerol. It then transforms fatty acids into acetyl coenzyme A ("acetyl-CoA") molecules, which are then eventually transformed through ketogenesis into the water-soluble ketone bodies beta-hydroxybutyrate ("β-hydroxybutyrate" or "BHB"), acetoacetate, and acetone in the liver. BHB and acetoacetate are the ketone bodies used by the body for energy while acetone is removed as a by-product of ketogenesis. Although BHB is technically not a ketone, it is still commonly referred to as a "ketone body" in the context of ketosis.

The metabolism of ketone bodies is associated with several beneficial effects. However, despite the many health advantages of pursuing a ketogenic diet or lifestyle and maintaining a state of nutritional ketosis, there remain significant barriers to pursuing and maintaining a ketogenic state. One of these barriers is the difficulty of transitioning into a ketogenic state. The fastest endogenous way to entering ketosis is to adopt a catabolic state through depleting glucose stores in the body through fasting combined with high intensity exercise. This will deplete the body's limited glucose and glycogen stores. This is physically and emotionally demanding and is extremely challenging even for the most motivated and disciplined.

Additionally, the transition into ketosis is often accompanied by hypoglycemia which can cause lethargy and light-headedness in many, resulting in an uncomfortable physiological and mental state commonly referred to as the "low-carb flu" or "keto flu." Many people also experience a down-regulation in their metabolism as the body goes into an "energy-saving" mode. Some suggest that these transitory symptoms may last as long as two to three weeks. During this transition period, if any meal or snack consisting of carbohydrates over the restrictive amount is consumed, there is a rapid termination of ketogenesis, causing the body to exit from its state of ketosis as the body shifts back to glucose utilization as its primary fuel. At this point, the difficult transition into ketosis must begin anew. Thus, despite the potential of a ketogenic diet for weight loss and other health benefits, serious limitations continue to hinder the full realization of its potential.

Intermittent Fasting

A method of fasting commonly referred to as "intermittent fasting" has increased in popularity in recent years as an alternative to long-term fasting. Because prolonged fasting is difficult and not fully sustainable over the long term, intermittent fasting attempts to provide many of the same benefits of fasting while minimizing the associated drawbacks. Although intermittent fasting, like prolonged fasting, involves entering into a catabolic state, but intermittent fasting shortens the window of time within the day in which eating is allowed. For example, with a regular eater, there are about 16-18 hours between the time the first and last quantities of food are eaten. Intermittent fasting seeks to shorten this eating window. Intermittent fasting regimens vary, but all typically attempt to shorten the eating window to a time period of about 2-12 hours, more commonly about 4-10, rather than the typical 16-18.

Intermittent fasting provides similar benefits to prolonged fasting and nutritional ketosis. Although the fasting period in intermittent fasting typically does not last long enough for the user to completely deplete glycogen stores, ketosis typically begins to some degree after only about 12 hours of fasting. Intermittent fasting thus functions to train the body to utilize fat for energy, even if only for a few hours each day. In other words, as the body becomes more accustomed to longer periods of time between eating windows, it will become more metabolically flexible and able to more efficiently shift toward utilizing fats as a fuel source.

Intermittent fasting is also a popular regimen among athletes or those attempting to train specifically to achieve fat loss and achieve higher lean to fat mass ratios. Many schedule training sessions during the fasting period to more quickly deplete glycogen stores and thus accelerate or extend the fat burning window or to take advantage of beneficial hormone profiles during the fasting period. For example, many athletes may schedule training/workouts near the end of the fast when glycogen stores are more depleted and the body is metabolically shifted more towards a fat-burning state.

Hydroxymethyl Butyrate

Beta-hydroxy-beta-methylbutyrate, also known as hydroxymethyl butyrate or simply HMB, is a metabolite of leucine that has been used by bodybuilders and other athletes to promote muscle hypertrophy. HMB appears to consistently attenuate muscle catabolism in situations where muscle atrophy would be expected.

HMB is believed to function as a precursor to HMG-coenzyme A reductase, the rate limiting enzyme to cholesterol synthesis, an inhibitor of the ubiquitin-proteasome proteolytic pathway responsible for the degradation of intracellular proteins, and a protein synthesis promoter via an mTOR dependent mechanism. HMB is also believed to induce muscle proliferation via the MAPK/ERK pathway (Kornasio R, et al. "Beta-hydroxy-beta-methylbutyrate (HMB) stimulates myogenic cell proliferation, differentiation and survival via the MAPK/ERK and PI3K/Akt pathways" Biochim Biophys Acta (2009)) and/or mTOR pathway (Pimentel G D, et al. "β-Hydroxy-β-methylbutyrate (HMβ) supplementation stimulates skeletal muscle hypertrophy in rats via the mTOR pathway" Nutr Metab (Lond) (2011)).

HMB may also reduce apoptosis of myocytes (Kornasio R, et al.) which tends to increase during catabolism associated with aging and cachexia. HMB supplementation can enhance levels of ATP and glycogen in skeletal muscle (Pinheiro C H, et al. "Metabolic and functional effects of beta-hydroxy-beta-methylbutyrate (HMB) supplementation in skeletal muscle" Eur J Appl Physiol (2012)). HMB has been noted to potentially reduce creatine kinase levels following exercise (a marker of muscle damage) in trained males (Wilson J M, et al. "β-Hydroxy-β-methylbutyrate free acid reduces markers of exercise-induced muscle damage and improves recovery in resistance-trained men" Br J Nutr (2013)). HMB may also aid in attenuating soreness following weightlifting (van Someren K A et al. "Supplementation with beta-hydroxy-beta-methylbutyrate (HMB) and alpha-ketoisocaproic acid (KIC) reduces signs and symptoms of exercise-induced muscle damage in man" Int J Sport Nutr Exerc Metab (2005)).

HMB is conventionally provided as either a calcium salt or the free acid form. The free acid form is believed to have somewhat greater bioavailability, with higher $C_{max}$ and area under the curve (AUC), though the calcium salt is believed to remain in the body for longer periods of time. All endogenous HMB is derived from dietary leucine, and HMB levels are therefore correlated with dietary leucine intake, with only about 5% of all leucine oxidation in vivo resulting in HMB formation. An issue with calcium HMB is its low absorption in at least some individuals. To improve absorption, other salts may be preferred, in addition to the free acid form, such as sodium HMB, potassium HMB, magnesium HMB, and amino acid salts of HMB.

HMB supplementation has also been associated with reducing the rate of age-related motor decline in rats, even when lean mass is unaffected (Wilson J M, et al. Beta-hydroxy-beta-methyl-butyrate blunts negative age-related changes in body composition, functionality and myofiber dimensions in rats; J Int Soc Sports Nutr (2012)).

Accordingly, HMB supplementation has been studied for a variety of biological effects, and while positive results have often been noted, the effects typically appear to be relatively minor or somewhat inconsistent. Thus, although HMB supplementation appears to have great potential for achieving various health benefits, there is an ongoing need for determining bio-mechanisms, compositions and methods capable of utilizing and/or enhancing the effects of HMB to levels that can significantly benefit health.

SUMMARY

Disclosed herein are compositions that include a combination of: (1) beta-hydroxy-beta-methylbutyrate ("HMB"); (2) a ketone body ("KB") component such as beta-hydroxybutyrate ("BHB") and/or acetoacetate ("AcAc"); and (3) optionally a dietetically or pharmaceutically acceptable carrier. For ease of reference, such combination compositions may be referred to herein as "KB-HMB", "HMB-KB", or, in the case where the KB component is primarily or exclusively BHB, "HMBHB".

Also disclosed herein are methods of using such compositions for promoting body composition restructuring, primarily an increase in a person's lean-to-fat mass ratio. It has been found that combining a ketone body component and HMB results in a more rapid change in the lean-to-fat ratio compared to conventional compositions and methods for increasing lean-to-fat mass ratio. For example, the compositions described herein may be beneficially utilized to help the user achieve (e.g., simultaneously) an anabolic state with respect to muscle and a catabolic state with respect to fat, which has not been thought to be possible according to conventional training protocols.

There are essentially three ways to increase lean-to-fat mass ratio: (1) increasing muscle mass while maintaining or only marginally increasing fat mass; (2) reducing fat mass while maintaining or only marginally reducing muscle mass; and (3) a combination of the two in which muscle mass is increased while fat mass is reduced. The compositions and methods disclosed herein can be used to achieve any or all three of these in a mammal depending on preference and regimen.

Loss of lean muscle mass is often associated with fasting and/or a ketogenic diet. Simply put, it is difficult for the body to build or even preserve muscle while also losing fat.

Generally, the body is either in an overall anabolic state where both muscle and fat are gained, or an overall catabolic state where both muscle and fat are reduced. Changing body composition using conventional training and dieting protocols requires sequentially planned processes where a person must concentrate on multiple stages of muscle building and fat loss in order to achieve desired results. This requires significant time, discipline, and often requires an amount of trial and error to get it right. In contrast to conventional training and dieting protocols, the compositions and methods described herein can effectively and consistently increase the lean-to-fat mass ratio regardless of whether the goal is to build muscle mass, reduce fat mass, or a combination thereof.

Moreover, as compared to conventional "bulking" and "cutting" cycles, compositions described herein assist in achieving a desired body composition much faster and with less required swings in overall body weight. This is possible because the described compositions eliminate the need to "overshoot" during a bulking phase and then shift to a completely opposite catabolic regimen to cut gained fat. There are at least some circumstances where use of the KB-HMB compositions can provide increases in muscle mass equal to or greater than a traditional bulk phase protocol and/or where use of the KB-HMB compositions can provide fat loss equal to or greater than a traditional cut phase protocol. However, even if muscle increase and/or fat loss are somewhat slower while using KB-HMB compositions as compared to respective bulking and cutting protocols, the desired end result can still be achieved much faster through use of KB-HMB compositions. For example, even if muscle gains could be somewhat slower while using the KB-HMB compositions than during a traditional "bulk" phase and/or if fat loss could be somewhat slower while using the KB-HMB compositions than during a traditional "cut" phase, avoiding the need to do two completely different extremes leads overall to a significantly faster route to desired results.

Using the KB-HMB compositions as disclosed herein provides a simplified way of more quickly and predictably achieving the same or better results provided by staged bulking and cutting cycles. Not only do the KB-HMB compositions provide superior results for those already used to bulking and cutting cycles, it opens up the process of successful body composition shaping to the majority of people who do not have the time, discipline, or desire to perform staged bulking and cutting cycles wish while achieving similar results. There are many people outside of the bodybuilding community who will now be able to engage in body composition shaping without having to develop the discipline of a body builder.

The ability of the KB-HMB compositions to promote both the anabolic buildup of lean muscle mass and the catabolic reduction of fat means the body can be in both an anabolic and catabolic state at the same time, or in a "catanabolic state" where the body is both building muscle and cutting fat at the same time.

In some applications, the compositions and methods may be utilized to augment the benefits of ketosis and fasting while minimizing undesirable side effects such as lack of energy and loss of muscle mass. Although the beneficial effects of the compositions and methods may often be described herein as being associated with ketosis and/or fasting, users may still benefit from the compositions even if not necessarily in a fasting or ketogenic state and maintain an anabolic energy state.

The ketone body component provides an exogenous source of ketone bodies that can be utilized by the body for energy without significantly causing the user to "break" the fast (e.g., will not cause a significant increase in blood insulin levels) and thereby lose the hard-earned physiological benefits of the fasted state. The ketone body component is also beneficial for users who train during the fasting period. While this is the period where fat burning is optimized, it can make training difficult because of relatively low levels of energy and motivation. The energy provided by the ketone body component can help the user more effectively train with minimal disruption of the fasted state.

The ketone body component can also aid in inducing and sustaining a state of ketosis in the subject. For example, the ketone body component can help the body more quickly shift toward a fat-burning catabolic state. This can be particularly helpful during intermittent fasting, where the fat burning window at the end of the fasting period is relatively short.

Moreover, even where a user is not necessarily in a fasted state, exogenous ketone body supplementation can benefit the user by aiding mitochondrial function while preserving blood glucose levels and glycogen stores, which then remain available for anabolic building of lean muscle as a result of exercise. This permits glucose, protein, and insulin to work together to build lean muscle mass when called upon rather than be burned as energy sources. In addition, because excess ketones, unlike sugars, are not converted into fat, they do not cause the simultaneous buildup of fat and muscle as when consuming a normal caloric intake of sugar, protein and fat.

The HMB component beneficially augments the effects of the ketone body component and functions to reduce undesired loss of muscle mass. Unexpectedly, it has now been found that the combination of BHB and HMB in proper quantities and/or ratios provides for a rapid increase in the lean-to-fat mass ratio at a rate that would not have been predicted based on the individual effects of these components when used in isolation. For example, supplementation of a KB-MHB composition can lead to muscle mass building coupled with limited or no fat gain, fat loss coupled with limited muscle wasting, or even lean mass building coupled with fat loss. The effects on lean-to-fat mass ratio are greater than the expected additive effects resulting from supplementation with either BHB alone or HMB alone. In addition, increasing the lean-to-fat mass ratio can be achieved in a much shorter time period.

The term "lean mass" is conventionally understood to encompass all non-fat mass of an individual. This includes water weight and non-muscle tissue weight. Although an individual's lean mass can therefore technically fluctuate based on a variety of measures that do not directly relate to muscle mass, most notably fluctuations in hydration levels, the changes in lean mass described herein refer to more long-term changes in skeletal muscle mass and not the less relevant fluctuations related to water weight or non-muscle tissue weight. Accordingly, lean mass may sometimes be referred to herein as simply "muscle mass" or similar term.

The KB-HMB compositions described herein may be provided in various forms, such as one-part or multi-part compositions configured for administration by one or more of ingestion, intragastric, injection, topical application, inhalation, oral mucosal administration, rectal administration, vaginal administration, or parenteral administration.

Additional features and advantages will be set forth in part in the description that follows, and in part will be obvious from the description, or may be learned by practice of the embodiments disclosed herein. It is to be understood that both the foregoing brief summary and the following detailed description are exemplary and explanatory only and are not restrictive of the embodiments disclosed herein or as claimed.

DETAILED DESCRIPTION

I. Definitions

A. Compounds

Figure 1:
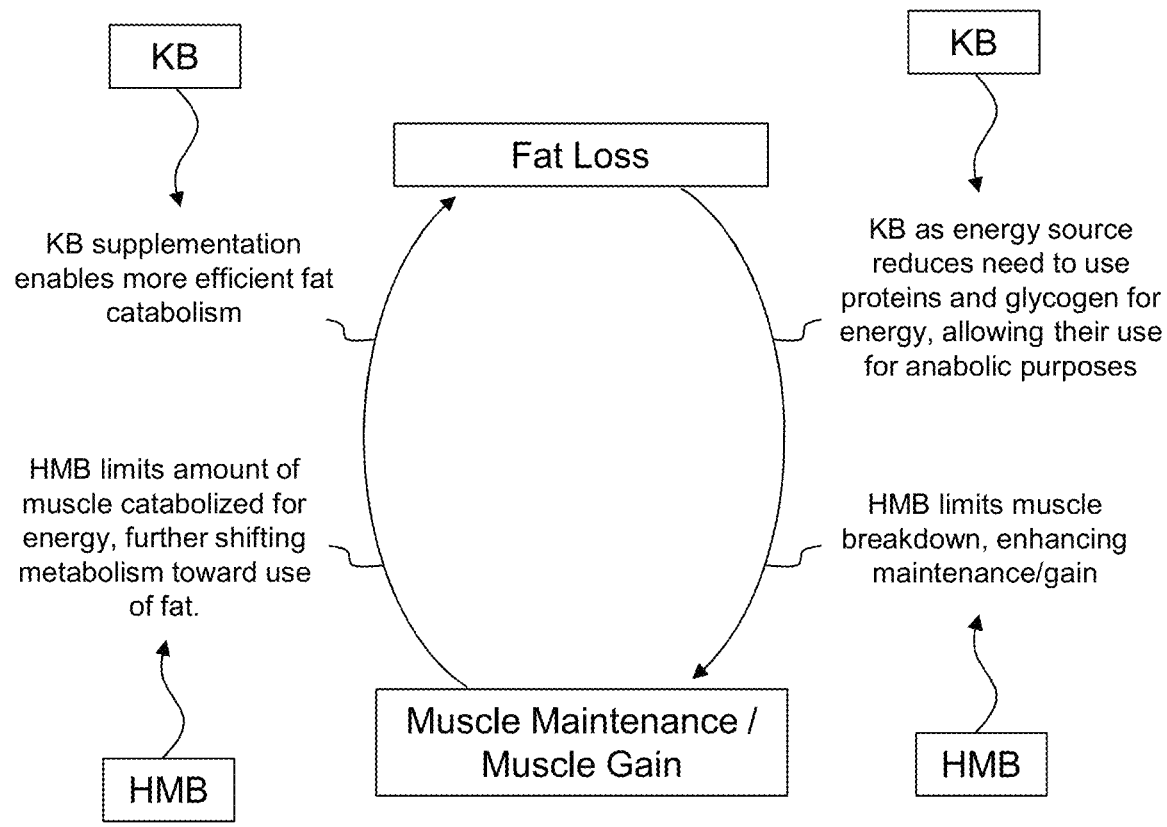
FIG. 1 schematically illustrates the mutually augmenting effects of a ketone body component (such as BHB) and HMB for the dual benefits of muscle maintenance (or even muscle gain) and fat loss.

The compound "beta-hydroxy-beta-methylbutyrate", "hydroxymethyl butyrate", or "HMB" has the structure of Formula I:

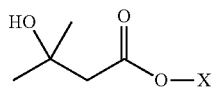

Formula I where, X can be hydrogen, metal ion, amino cation such as from an amino acid, alkyl, alkenyl, aryl, or acyl.

When X is a hydrogen, the compound is hydroxymethyl butyric acid. When X is a metal ion or an amino cation, the compounds is a hydroxymethyl butyrate salt. When X is alkyl, alkenyl, aryl, or acyl, the compounds is a hydroxymethyl butyrate ester.

As shown, HMB has a butyrate backbone and is therefore structurally similar to ketone bodies such as acetoacetate and particularly BHB. Without being bound to any particular theory, it is believed that the structurally similar but still unique features of the two components may underlie some of the observed synergistic effects of the combination compositions described herein. For example, though HMB and ketone bodies provide different functional effects upon administration, there may be enough structural and/or functional crossover to allow mutual enhancement of each type of compound via molecular signaling, conversion pathways, or other mechanism.

The term "ketone body" refers to compounds capable of being utilized by the body as an energy source and includes the compounds beta-hydroxybutyrate (BHB) and acetoacetate. Ketone body precursors may additionally or alternatively be utilized in the compositions described herein. Suitable ketone body precursors include, but are not limited to, 1,3-butanediol, medium chain fatty acids, and esters of medium chain fatty acids such as medium chain triglycerides. Ketone body compounds and ketone body precursor compounds are described in more detail below.

The compound "beta-hydroxybutyrate," also known as β-hydroxybutyrate, 3-hydroxybutyrate, βHB, or BHB, is the deprotonated form of beta-hydroxybutyric acid, which is a hydroxycarboxylic acid having the general formula $CH_3CH_2OHCH_2COOH$. The deprotonated form present at typical biological pH levels is $CH_3CH_2OHCH_2COO^-$. The general chemical structure of Formula II represents BHB compounds that may be utilized in the disclosed compositions (conformational isomers thereof may also be utilized):

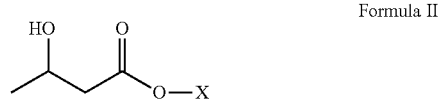

Formula II where X can be hydrogen, metal ion, amino cation such as from an amino acid, alkyl, alkenyl, aryl, or acyl.

When X is a hydrogen, the compound is beta-hydroxybutyric acid. When X is a metal ion or an amino cation, the compounds is a beta-hydroxybutyrate salt. When X is alkyl, alkenyl, aryl, or acyl, the compounds is a beta-hydroxybutyrate ester. The foregoing compounds can be in any desired physical form, such as crystalline, powder, solid, liquid, solution, suspension, or gel.

Unless otherwise specified, the term "salt" does not mean or imply any particular physical state, such as a crystalline, powder, other solid form, dissolved in water to form a liquid solution, dispersed in a liquid to form a suspension, or gel. A salt can be formed in solution, such as by at least partially neutralizing beta-hydroxybutyric acid with a strong or weak base, such as an alkali or alkaline earth metal hydroxide, carbonate, or bicarbonate, basic amino acid, and the like.

Beta-hydroxybutyrate (BHB) is utilized by a patient's body as an energy source during instances of low glucose levels in the subject or when a patient's body is supplemented with a usable form of BHB. Although not technically a "ketone", one of skill in the art will recognize that BHB, in the context of ketosis, is commonly referred to as a "ketone body" because of its close relationship to and biological interplay with acetoacetate, which is a true ketone.

BHB is a chiral compound and can exist as the R-enantiomer or the S-enantiomer, a racemic mixture, or a mixture where one of the enantiomers is enriched relative to the other. Endogenous BHB produced by the body is the R-enantiomer and therefore the form that is more readily available as a ketone body. BHB can be transformed by the body into acetoacetate, which is another ketone body utilized by the body but is not chiral, and acetoacetate can be transformed by the body into the R-enantiomer. It is believed that the S-enantiomer of BHB can be transformed into the R-enantiomer by first being converted into acetoacetate and then into the R-enantiomer, or the body can utilize the acetoacetate directly. The S-enantiomer may also be highly bioactive in its own right, although only a small amount of the S-enantiomer is produced by the body.

The compound "acetoacetate" ("AcAc"), is a true ketone and the deprotonated form of acetoacetic acid, which is a carboxylic acid having the formula $CH_3COCH_2COOH$. The deprotonated form present at typical biological pH levels is therefore $CH_3COCH_2COO^-$. As stated above, the body can transform BHB into acetoacetate and vice versa. As with BHB, acetoacetate may be utilized as an energy source during ketosis or when a patient's body is supplemented with a usable form of acetoacetate regardless of the body's state of energy utilization preference. The general chemical structure of Formula III represents acetoacetate compounds that may be utilized in the disclosed compositions (conformational isomers thereof may also be utilized):

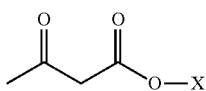

Formula III where X can be hydrogen, metal ion, amino cation, such as from an amino acid, alkyl, alkenyl, aryl, or acyl.

As with BHB, acetoacetate may be utilized by a patient's body as an energy source during instances of low glucose levels in the subject or when a patient's body is supplemented with a usable form of acetoacetate. Unlike BHB, acetoacetate is a true "ketone", and in the context of ketosis is commonly referred to as a "ketone body" along with BHB.

The beta-hydroxybutyrate and acetoacetate compounds described above may be collectively referred to herein as "ketone bodies," "exogenous ketone bodies," a "ketone body component," or "exogenous ketones."

B. Stacked Forms & Mixed Cation Salts

The terms "stacked composition," "keto-stack," "stack," "ketone body stack," and variations thereof are used herein to refer to a composition including at least two separate compounds selected from the group consisting of: (i) a beta-hydroxybutyrate salt; (ii) an acetoacetate salt; (iii) an HMB salt; (iv) a beta-hydroxybutyrate ester; (v) an acetoacetate ester; (vi) an HMB ester; (vii) a beta-hydroxybutyrate free acid (i.e., beta-hydroxybutyric acid); (viii) an acetoacetate free acid (i.e., acetoacetic acid); and (ix) an HMB free acid (i.e., beta-hydroxy-beta-methyl butyric acid).

A stacked composition may include a combination of compounds selected from (i) through (ix) such that there are at least two of (A)-(C), where: (A) represents one or more salts; (B) represents one or more esters; and (C) represents one or more free acids.

Exemplary salt forms include sodium, potassium, calcium, magnesium salts, and lithium. Some embodiments include one or more transition metal salts. Transition metal cations suitable for use as part of a salt include chromium, manganese, cobalt, copper, zinc, iron, (e.g., as an iron II or iron III cation), molybdenum, and selenium. Other suitable salt forms include cations of organic compounds capable of having a net positive charge, including amino acids or their derivatives/metabolites such as arginine, lysine, leucine, iso-leucine, histidine, ornithine, creatine, agmatine, L-glutamine, and citrulline.

Suitable ester forms include mono-esters of ethanol, mono-esters of 1-propanol, mono-esters of 1,3-propanediol, di-esters of 1,3-propanediol, mono-esters of S-1,3-butanediol, mono-esters of R-1,3-butanediol, di-esters of 1,3-butanediol, mono-esters of glycerin, di-esters of glycerin, and tri-esters of glycerin. 1,3-butanediol is a metabolic BHB precursor that may be additionally or alternatively be utilized as a source of BHB and/or acetoacetate compounds. The acid forms typically have an unpleasant taste but can be used by appropriate taste masking mechanisms, such as one or more capsules, tablets, or other bolus.

Each of the different forms (salt, acid, ester) has its own properties and its own potential benefits and limitations. For example, ester forms of beta-hydroxybutyrate typically have poor organoleptic properties relative to the other forms of beta-hydroxybutyrate. That is, ester forms of beta-hydroxybutyrate are often described as having a pungent taste and/or smell.

Salt forms are generally considered to taste better than ester forms. However, administration of clinically or dietetically effective doses of ketone bodies and HMB in salt form inherently requires administration of relatively high levels of the corresponding cations. Sodium, for example, is often used as the cation in beta-hydroxybutyrate salts, and high levels of sodium have well-known negative health effects. By way of further example, calcium is often used as the cation in HMB salts, and high levels of calcium can also be detrimental to health, particularly when not balanced by other cations. Although different salts having different cations may be mixed to dilute the impact of a single cation, it can still be difficult to provide effective amounts of ketone bodies and HMB without upsetting the electrolyte balance in the subject.

The free acid forms of beta-hydroxybutyrate (i.e., beta-hydroxybutyric acid), acetoacetate (i.e., acetoacetic acid), and HMB (i.e., hydroxymethyl butyric acid) may also be utilized. However, because of the relatively low pKa values (e.g., beta-hydroxybutyric acid has a pKa of 4.70), these compounds deprotonate and produce $H^+$ at physiological pH. The resulting excess acidity can cause undesirable side effects including causing or aggravating gastrointestinal issues such as ulcers or reflux.

Combining or stacking different salt types and/or different forms of ketone bodies and HMB can beneficially limit the occurrence or severity of these undesirable side-effects and/or can permit administration of higher doses. For example, a mixed salt composition comprising different cations or a stacked form can deliver the same amount of ketone bodies and HMB as a single form without causing the same occurrence and/or severity of side-effects. Likewise, a mixed salt for or a stacked form can deliver a greater amount of ketone bodies and HMB than a single form before reaching similar occurrence and/or severity of side-effects.

In other words, for a given dose of ketone bodies and HMB, a stacked form is expected to have less 1) organoleptic side-effects, 2) electrolyte imbalance side-effects, and/or 3) acidity side-effects as compared to the single form. For example, a single form ester may have a threshold dosage that the typical user will not exceed because of the negative organoleptic side-effects, a single form salt may have a threshold dosage limited by the recommended dietary limits of the electrolytes administered with the salt, and a single form acid may have a threshold dosage that the typical user will not exceed because of the negative effects of acidity. The combined or stacked forms may allow supplementation of greater amounts of ketone bodies and HMB without exceeding any of the thresholds related to organoleptic, electrolyte, or acidity side-effects.

In some embodiments, the composition includes at least about 2% of ester forms, at least about 2% of salt forms, and at least about 2% of free acid forms on a molar basis. In other words, at least about 2% of the number of molecules (HMB, BHB, and/or acetoacetate) are provided by each separate form. More preferably, a composition includes at least about 5% ester form, at least about 5% salt form, and at least about 5% free acid form on a molar basis, or at least about 10% ester form, at least about 10% salt form, and at least about 10% free acid form on a molar basis, or at least about 20% ester form, at least about 20% salt form, and at least about 20% free acid form on a molar basis, or at least about 30% ester form, at least about 30% salt form, or at least about 30% free acid form on a molar basis.

In some embodiments, the composition includes an ester form at about 2% to about 96%, or about 5% to about 90%, or about 10% to about 80%, or about 20% to about 60% on a molar basis, includes a salt form at about 2% to about 96%, or about 5% to about 90%, or about 10% to about 80%, or about 20% to about 60% on a molar basis, and includes an acid form at about 2% to about 96%, or about 5% to about 90%, or about 10% to about 80%, or about 20% to about 60% on a molar basis.

C. Esters & Oligomers of BHB & HMB

It is also possible to form an ester between BHB and HMB, such as where the carboxyl group of a BHB molecule is esterified with the hydroxyl group of an HMB molecule. Alternatively, the carboxyl group of an HMB molecule can be esterified with the hydroxyl group of a BHB molecule. In practice, forming an ester between BHB and HMB results in both ester forms and possibly mixed oligomers.

Such ester forms of BHB and HMB can be used to provide a stabilized compound or oligomer with specific ratios of BHB and HMB. The ratio of BHB to HMB in the ester or oligomer compounds will largely depend on the stoichiometric ratio of BHB and HMB that are added to the esterification reaction mixture. In some embodiments, the ratio of BHB to HMB can be in a range of about 0.5:1 to about 5:1. The ester or oligomer can also be enriched with additional BHB and/or HMB molecules (e.g., free or salt forms or other ester forms) to readily provide other desired ratios of BHB to HMB.

Formula IV represents an exemplary BHB and HMB ester in which the carboxyl group of a BHB molecule is esterified with the hydroxyl group of an HMB molecule.

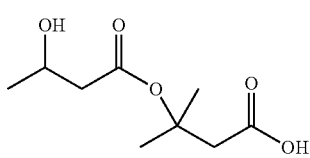

Formula IV

Formula V represents an exemplary BHB and HMB ester in which the hydroxyl group of a BHB molecule is esterified with the carboxyl group of an HMB molecule.

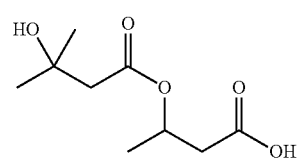

Formula V

Similarly, it is possible to form an ester between acetoacetate and HMB, where the carboxyl group of an acetoacetate molecule is esterified with the hydroxyl group of an HMB molecule. Formula VI represents an exemplary acetoacetate-HMB ester.

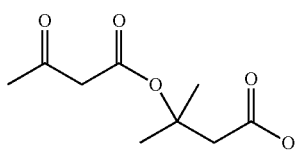

Formula VI

Providing the compound in an ester form may beneficially enhance the bioavailability of the compound. For example, the esterified forms of HMB as described herein may increase absorption relative to other forms of HMB, such as calcium HMB. Such esters may be formed using known esterification techniques such as, for example, Fischer esterification.

D. Mixed Anion Salts

Another way to increase the absorption and bioavailability of HMB is to provide one or mixed anion salt compounds, such as where a divalent cation forms a salt with a BHB anion and an HMB anion. Examples of divalent mixed anion salts include magnesium beta-hydroxybutyrate hydroxymethyl butyrate and calcium beta-hydroxybutyrate hydroxymethyl butyrate, or Mg(BHB)(HMB) and Ca(BHB)(HMB), respectively. Formula VII is the generic structure of these compounds.

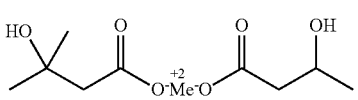

Formula VII where $Me^{+2}$ is $Mg^{+2}$ or $Ca^{+2}$.

Similarly, divalent mixed anion salts can include magnesium acetoacetate hydroxymethyl butyrate and calcium acetoacetate hydroxymethyl butyrate, or Mg(AcAc)(HMB) and Ca(AcAc)(HMB), respectively.

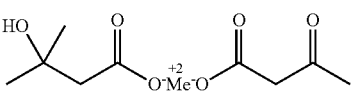

Formula VIII where $Me^{+2}$ is $Mg^{+2}$ or $Ca^{+2}$.

E. Other Definitions

The BHB compound can be provided as a racemic mixture of enantiomers, sometimes referred to DL-beta-hydroxybutyrate (alternatively RS-beta-hydroxybutyrate), which can be made synthetically. In humans, the enantiomer D-3-hydroxybutyrate ("D-beta-hydroxybutyrate", "D-BHB", "R-hydroxybutyrate" or "R-BHB") is synthesized in the liver from acetoacetate, the first ketone produced when in a state of ketosis. Therefore, it may be desirable to provide BHB as the enantiomer D-3-hydroxybutyrate to increase potency, either enriched relative to L-3-hydroxybutyrate ("L-beta-hydrobutyrate", "L-BHB", "S-beta-hydrobutyrate" or "S-BHB") or isolated from L-3-hydroxybutyrate. Alternatively, it may be desirable to provide BHB as the enantiomer L-3-hydroxybutyrate to increase potency, either enriched relative to D-3-hydroxybutyrate or isolated from D-3-hydroxybutyrate. Administering D-3-hydroxybutyrate, the endogenous form, results in attaining rapid elevated ketosis, while administering L-3-hydroxybutyrate, which must first be converted to acetoacetate, and then optionally to D-3-hydroxybutyrate, may provide slower and more sustained ketosis. D-3-hydroxybutyrate is also referred to as "R-beta-hydroxybutyrate" and L-3-hydroxybutyrate is also referred to as "S-beta-hydroxybutyrate."

As used herein, "subject," "patient," or "user" refers to mammals, including humans and other primates. The subject may be any mammal requiring metabolic therapy, treatment, or prophylaxis, or any mammal suspected of requiring metabolic therapy, treatment, or prophylaxis. Prophylaxis means that regiment is undertaken to prevent a possible occurrence, such as where a high risk of diabetes or other metabolic disorder is identified. "Patient," "subject," and "user" are used interchangeably herein.

"Ketosis" as used herein refers to the metabolic state entered during an intermittent fasting period or a longer fasting period (e.g., 2 days or more). A subject can also be considered to be in ketosis when the subject has blood ketone levels within the range of about 0.5 mmol/L to about 16 mmol/L. Ketosis may improve mitochondrial function, decrease reactive oxygen species production, reduce inflammation and increase the activity of neurotrophic factors. "Keto-adaptation" as used herein refers to prolonged nutritional ketosis (>1 week) to achieve a sustained nonpathological "mild ketosis" or "therapeutic ketosis," or it denotes an altered metabolism in which fat becomes the predominant energy source, consequently shifting the body from a state of fat storage to a state of fat oxidation. It is believed that administering ketone bodies in doses disclosed herein can provide the same or similar benefits as being in a state of ketosis even if the subject has not achieved a sufficiently high blood ketone level to technically be in a state of ketosis.

The term "administration" or "administering" is used herein to describe the process in which the disclosed compositions are delivered to a subject. "Administration" and "administering" can include any known method or configuration that can deliver the disclosed compositions to blood, tissues and/or cells, whether to a targeted region, widely diffused, or systemic.

The term "unit dose" refers to a dosage form that is configured to deliver a specified quantity or dose of composition or component thereof. Example dosage forms include, but are not limited to, tablets, capsules, powders, food products, food additives, beverages (such as flavored, vitamin fortified, or non-alcoholic), beverage additives (such as flavored, vitamin fortified, or non-alcoholic), candies, suckers, pastilles, food supplements, dietetically acceptable sprays (such as flavored mouth spray), injectables (such as an alcohol-free injectable), and suppositories. Such dosage forms may be configured to provide a full unit dose or fraction thereof (e.g., ½, ⅓, or ¼ of a unit dose).

Another dosage form that can be used to provide a unit dose of composition or component thereof is a unit dose measuring device, such as a cup, scoop, spatula, syringe, dropper, spoon, or colonic irrigation device, which is configured to hold therein a measured quantity of composition equaling a full unit dose or fraction thereof (e.g., ½, ⅓, or ¼ of a unit dose). For example, a bulk container, such as a carton, box, can, jar, bag, pouch, bottle, jug, or keg, containing several unit doses of composition (e.g., 5-250 or 10-150 unit doses) can be provided to a user together with a unit dose measuring device that is configured to provide a unit dose, or fraction thereof, of composition or component thereof.

A kit for use in providing a composition as disclosed herein in bulk form, while providing unit doses of the composition, may comprise a bulk container holding therein a quantity of composition and a unit dose measuring device configured to provide a unit dose, or fraction thereof, of composition or component thereof. One or more unit dose measuring devices may be positioned inside the bulk container at the time of sale, attached to the outside of the bulk container, prepackaged with the bulk container within a larger package, or provided by the seller or manufacture for use with one or multiple bulk containers.

The kit may include instructions regarding the size of the unit dose, or fraction thereof, and the manner and frequency of administration. The instructions may be provided on the bulk container, prepackaged with the bulk container, placed on packaging material sold with the bulk container, or otherwise provided by the seller or manufacturer (e.g., on websites, mailers, flyers, product literature, etc.) The instructions for use may include a reference on how to use the unit dose measuring device to properly deliver a unit dose or fraction thereof. The instructions may additionally or alternatively include a reference to common unit dose measuring devices, such as spoons, spatulas, cups, and the like, not provided with the bulk container (e.g., in case the provided unit dose measuring device is lost or misplaced). In such case, a kit may be constructed by the end user when following instructions provided on or with the bulk container, or otherwise provided by the seller regarding the product and how to properly deliver a unit dose of composition, or fraction thereof.

II. KB-HMB Compositions

KB-HMB compositions described herein may comprise: (1) a ketone body (KB) component such as beta-hydroxybutyrate (BHB) and/or acetoacetate (AcAc); (2) HMB; and (3) optionally a dietetically or pharmaceutically acceptable carrier.

A KB-HMB composition may also optionally include a supplemental source of ketone body precursors such as one or more of 1,3-butanediol, fatty acids, and/or esters of fatty acids. A typical ester form of fatty acids is a mono-, di-, or triglyceride. Preferred forms of fatty acids and their esters are medium chain fatty acids and medium chain triglycerides (MCT), though short and/or long chain fatty acids and their esters may also be utilized. In embodiments where used, a medium chain fatty acid has from 6 to 12 carbons, preferably from 8 to 10 carbons. Compositions and methods related to the combination of BHB with a medium chain fatty acid, or ester thereof, are disclosed in U.S. Pat. No. 9,138,420, which patent is incorporated herein by this reference in its entirety.

Exemplary medium chain fatty acids are caproic acid, also known as hexanoic acid having 6 carbons, caprylic acid, also known as octanoic acid having 8 carbons, capric acid, also known as decanoic acid having 10 carbons, and lauric acid, having 12 carbons. Because MCTs are ketone body precursors, including one or more MCTs may provide an additional source for the production of ketone bodies independent of the BHB and acetoacetate compounds, thus helping to promote sustained elevation of ketone levels to a desired therapeutic level.

The term "short chain triglycerides" (SCT) refers to molecules similar to MCT molecules but with short chain fatty acids (less than 6 carbon atoms in length) attached to the glycerol backbone. The term "long chain triglycerides" (LCT) refers to molecules similar to MCT molecules but with long chain fatty acids (more than 12 carbon atoms in length) attached to the glycerol backbone.

Examples and sources of the medium chain fatty acid, or an ester thereof such as a medium chain triglyceride, include coconut oil, coconut milk powder, fractionated coconut oil, palm oil, palm kernel oil, caprilic acid, isolated medium chain fatty acids, such as isolated hexanoic acid, isolated octanoic acid, isolated decanoic acid, medium chain triglycerides either purified or in natural form such as coconut oil, and ester derivatives of the medium chain fatty acids ethoxylated triglyceride, enone triglyceride derivatives, aldehyde triglyceride derivatives, monoglyceride derivatives, diglyceride derivatives, and triglyceride derivatives, and salts of the medium chain triglycerides. Ester derivatives optionally include alkyl ester derivatives, such as methyl, ethyl, propyl, butyl, hexyl, etc.

When medium chain fatty acids, fatty acid esters, or mono-, di- or triglycerides of medium chain fatty acids are provided, the composition is preferably administered such that the weight ratio of ketone bodies to medium chain fatty acid (or ester thereof) ranges from about 4:1 to about 1:4, or from about 2:1 to about 1:2, or from about 1.5:1 to about 1:1.5. The same ratios may be used when short chain fatty acids (or esters thereof) or long chain fatty acids (or esters thereof) are additionally or alternatively used.

In alternative embodiments, the compositions may further include one or more short and/or long chain fatty acids, fatty acid esters, or mono-, di- or triglycerides of short and/or long chain fatty acids in order to provide an additional source of ketone bodies for sustaining ketosis. In some embodiments, the composition is preferably administered such that the ratio of BHB/acetoacetate to medium, short and/or long chain fatty acid (or ester thereof) ranges from about 4:1 to about 1:4, or from about 2:1 to about 1:2, or from about 1.5:1 to about 1:1.5.

Examples of short chain fatty acids include acetic acid, propionic acid, butyric acid, isobutyric acid, valeric acid, and isovaleric acid. Examples of medium chain fatty acids include caproic acid, caprylic acid, capric acid, and lauric acid. Examples of long-chain fatty acids include myristic acid, palmitic acid, stearic acid, arachidic acid, behenic acid, lignoceric acid, cerotic acid, omega-3 fatty acids, omega-6 fatty acids, omega-7 fatty acids, and omega-9 fatty acids.

As described above, KB-HMB compositions may be formulated with various ratios of ketone body component to HMB. KB-HMB compositions may also be formulated with various ratios of different forms of ketone bodies to one another. That is, some embodiments may include a greater proportion of BHB relative to acetoacetate, whereas other embodiments may include a greater proportion of acetoacetate relative to BHB. For example, the BHB to acetoacetate ratio may be about 0.1:1, 0.25:1, 0.5:1, 0.75:1, 1:1, 1.25:1, 1.5:1, 2:1, 4:1, 9:1, or may be within a range having any two of the foregoing ratios as endpoints. The ratio may be formulated according to particular application needs and preferences. For example, compositions using BHB as the ketone body component are believed to have greater relative effect on metabolic activity (e.g., fat loss, anti-inflammation, vasodilation) while compositions using acetoacetate as the ketone body component are believed to have greater relative effect on neurological activity (e.g., neuroprotection, anxiolytic and anti-depressant effects, memory).

Thus, where the primary intended effects are metabolic in nature, a KB-HMB composition may be formulated so that the BHB component makes up at least about 50%, or at least about 75%, or at least about 95%, or even about 100% of the content of the ketone body component. On the other hand, where the primary intended effects are neurological in nature, a KB-HMB composition may be formulated so that acetoacetate makes up at least about 50%, or at least about 75%, or at least about 95%, or even about 100% of the content of the ketone body component.

III. Treatment Effects

The administration of a KB-HMB composition may provide a variety of beneficial physiological effects, including one or more of muscle sparing or building, fat loss, appetite suppression, antioxidant effects, neuroprotection, memory enhancement, anxiety mediation, suppression of depressive symptoms, analgesic effects, anti-inflammatory effects, cardiovascular benefits (e.g., vasodilation and blood pressure modulation), anti-aging/longevity, anti-tumorigenic effects, and sleep enhancement, for example.

Though a variety of different pharmacological and/or physiological variables may be involved, the combination compositions described herein may enable complementary enhancement of several different physiological systems. Without being bound to any particular theory, it is presently believed that the HMB component functions to enhance the subject's ability to maintain or even build muscle mass while the exogenous ketone body component functions to promote fat loss and to further modulate and/or complement the effects of HMB via metabolic activity and/or molecular signaling, resulting in synergistically enhanced effects not capable with either component independently.

The beneficial treatment effects described herein may be achieved or enhanced as a result of supplementation with a KB-HMB composition. Although many of the examples are described in the context of a subject being in a state of ketosis, it will be understood that realization of the beneficial effects does not necessarily require the subject to be in a state of ketosis. In other words, beneficial effects may be realized as a result of co-administration of the exogenous ketone body component and the HMB. These effects may be further enhanced once the subject enters an active state of ketosis, and the exogenous ketone body component can itself aid in getting the subject into such a state, but ketosis is not necessarily a requirement for realizing these effects.

A. Fat Loss & Muscle Maintenance/Gain

Without being bound to any particular theory, FIG. 1 schematically illustrates a "positive feedback loop" that may underlie the synergistic effects for both fat loss and muscle maintenance and/or gain when a ketone body component ("KB" in the Figure) and HMB are co-administered in proper quantities and/or ratios. As shown, one of the primary effects of the KB is to promote fat loss by promoting ketosis and more efficient fat catabolism where molecules such as BHB are used by the body as a major energy source. With respect to muscle maintenance/gain, when KB is used as an energy source, it also reduces the need to use other molecules such as proteins and glycogen for energy, allowing them to be used instead for anabolic purposes such as muscle maintenance and growth.

One of the primary effects of HMB is to preserve muscle mass. By limiting the breakdown of muscle tissue, the ability to maintain and gain muscle is increased. With respect to fat loss, HMB limits the amount of muscle catabolized for energy, further shifting metabolism toward the use of fat.

While the above-described effects of KB and HMB are independently desirable, it has been surprisingly found that the combination of HMB and KB surprisingly enhances the fat loss effects and muscle maintenance/gain effects. For example, because the HMB functions to prevent muscle breakdown, less muscle is catabolized to supply the body's energy needs, further shifting metabolism toward fat catabolism and fat loss. At the same time, because the KB promotes more efficient use of fat for energy purposes, there is greater energy via available ketone bodies and less pressure for the body to catabolize muscle for its energy needs, thereby enhancing the muscle maintenance effects and ability to gain muscle. The positive feedback thus functions to promote muscle anabolism, which augments efficient fat loss, which further promotes muscle anabolism, which further augments efficient fat loss. The result is that both fat loss and muscle maintenance are synergistically enhanced via the combination composition.

HMB, being similar in chemical structure and engaging in some metabolic pathways similar to ketone bodies, is believed to have enhanced pharmacokinetics (e.g., more effective absorption, transport, cell permeation, etc.) when the subject is actively utilizing ketone bodies as an energy source, particularly when the subject is in a state of ketosis as opposed to a regular state of (primarily) glycolysis. For example, administration of HMB to a subject in combination with exogenous ketone bodies, where preferably the subject is also in a state of elevated and/or sustained ketosis as a result of supplementation with the ketone bodies, may result in about 10%, 20%, 40%, or 75% or more effective utilization of the HMB as compared to HMB supplementation without a ketone body component. Ketone bodies, in particular BHB, are potent free radical scavengers and provide direct antioxidant effects. Reducing free radical burden can also aid in promoting muscle building.

Figure 2A:
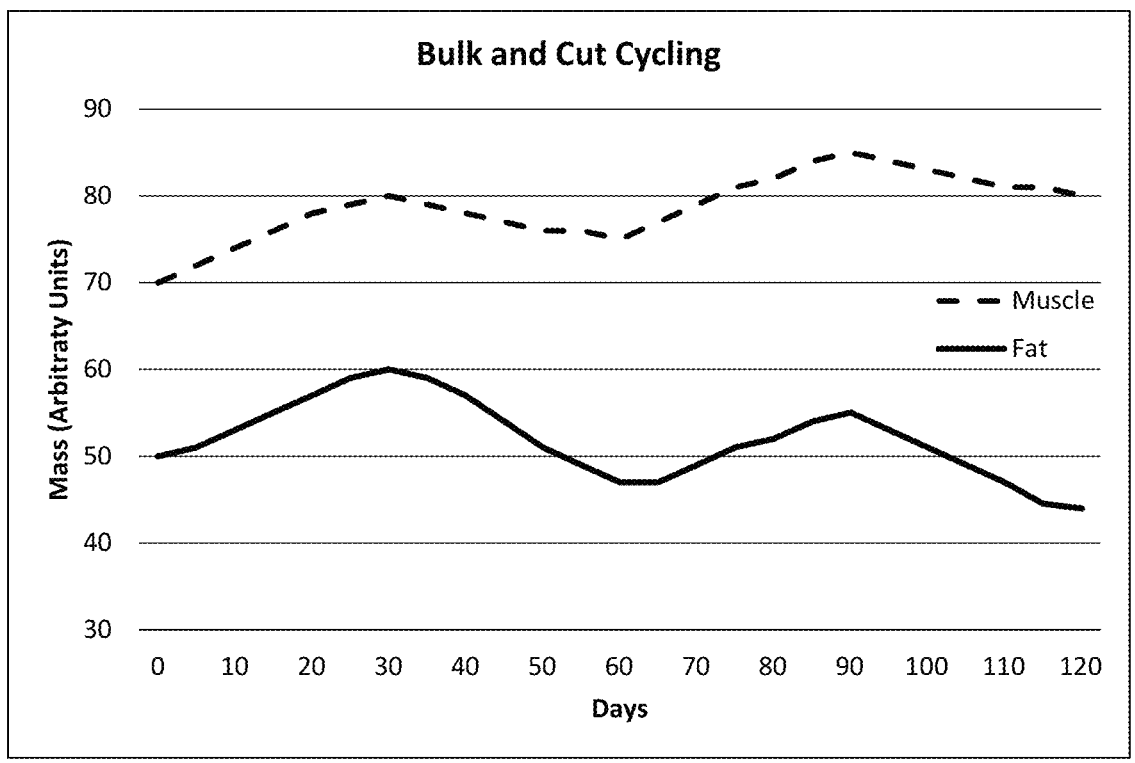
FIGS. 2A and 2B compare the expected change in muscle and fat mass of a subject during a conventional "bulk" and "cut" cycling protocol (FIG. 2A) and during a "catanabolic" protocol (FIG. 2B)
Figure 2B:
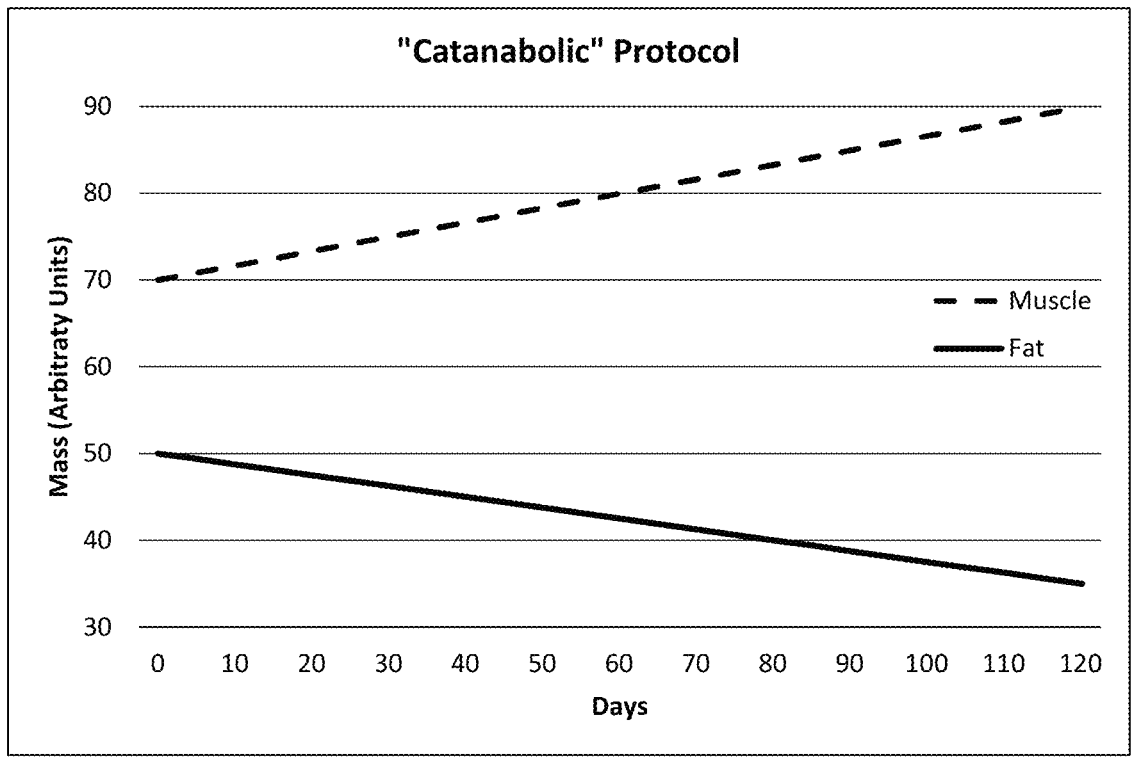

FIGS. 2A and 2B compare the expected change in muscle and fat mass of a subject during a conventional "bulk" and "cut" cycling protocol (FIG. 2A) and during a "catanabolic" protocol (FIG. 2B). The conventional approach to improving body composition involves a bulk phase where both muscle and fat are increased, followed by a cut phase where both muscle and fat are lost. The hope is that somewhat more muscle is gained than fat during the bulk phase, and/or that somewhat more fat is lost than muscle during the cut phase, so that at the end of a cycle there is a net improvement in the ratio of lean mass to fat mass.

As shown in FIG. 2A, after a first bulk phase (e.g., at 30 days) there are increases in both muscle and fat mass. During the subsequent cut phase (e.g., at 60 days), a lot of fat is lost, but it comes at the expense of losing a significant portion of the muscle gained in the bulk phase, and most of the fat loss is simply to undo fat increases associated with the bulk phase.

Although this type of cycling can lead to improved body composition over time (as shown by the increasing gap between the muscle and fat lines of the graph), it requires iteratively "overshooting" of both muscle gains and fat losses to make up for the expected backsliding that happens during opposing phases. This approach is inefficient, difficult for the user to follow, and involves significant swings in metabolism that can be damaging to health.

FIG. 2B illustrates the expected change in muscle and fat mass following a catanabolic protocol involving supplementation with a KB-BHB composition. Here, the user does not need to experience the extreme metabolic and dietary swings associated with bulking and cutting. Rather, the user progresses by increasing muscle mass and losing fat mass simultaneously. Even if the changes to muscle or fat mass are somewhat slower than during a bulk or cut phase, respectively, the overall net effects on muscle gain and fat loss are improved. In other words, even if muscle gains are somewhat slower during the catanabolic protocol than in a true bulk phase, the catanabolic protocol is not increasing fat along with the muscle, as with the bulk phase. Likewise, even if the rate of fat loss is somewhat slower during the catanabolic protocol than during a true cut phase, the catanabolic protocol is not losing muscle along with the fat, as with the cut phase.

Thus, even though conventional bulk/cut cycling oscillates between rapid muscle gain and rapid fat loss, the catanabolic protocol provides overall more rapid change in body composition. For example, comparing the results of the catanabolic protocol and the conventional bulk and cut cycling protocol after a full cycle (e.g., at 60 days), shows that the user can be expected to gain some muscle and lose some fat using bulking/cutting, but that the net effects on both muscle gain and fat loss are greater using the catanabolic protocol.

Further, the catanabolic protocol is expected to be easier for the user to follow and also avoids potential problems associated with big swings in metabolism. For example, while a bulk/cut cycle involves a period of caloric surplus followed by a period of caloric deficit, a user following the catanabolic protocol can be carried out while the user aims for a maintenance calorie diet. Of course, this could be modified in one direction or the other depending on particular user goals, but need not require the type of swings involved with a bulk/cut cycle.

Figure 3:
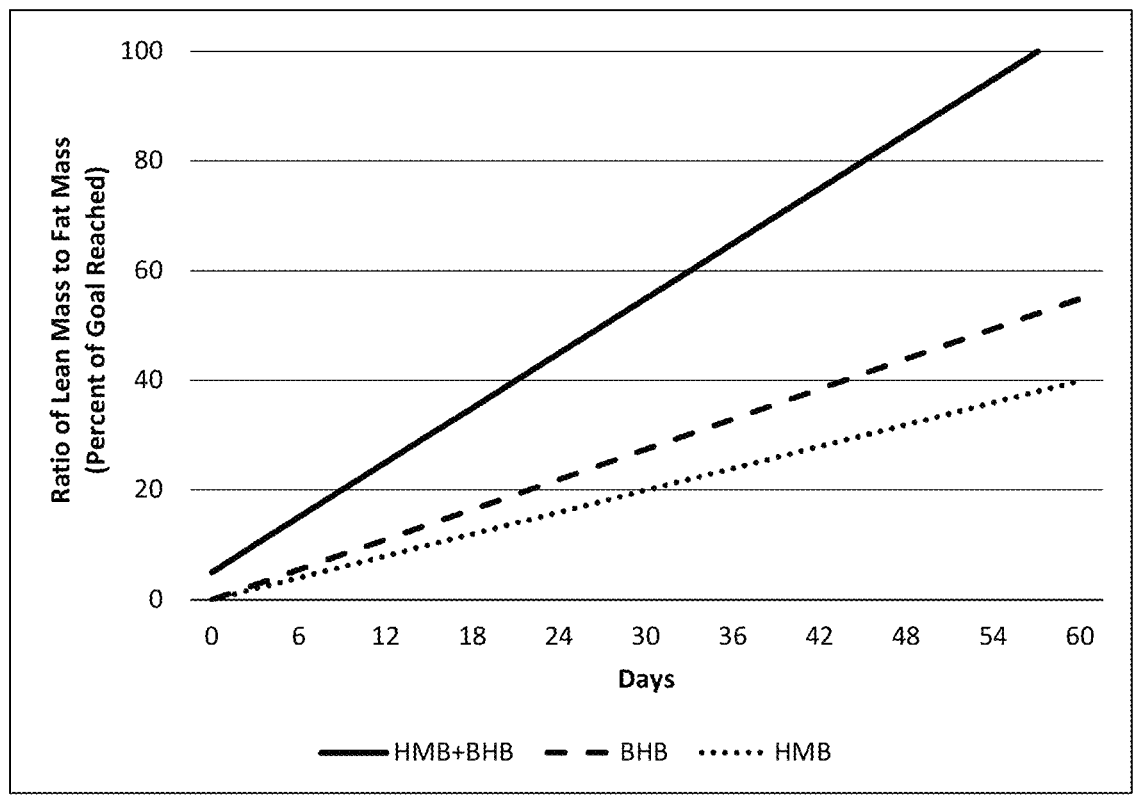
FIG. 3 illustrates expected changes to lean-to-fat mass ratios, relative to a given goal, resulting from different respective treatments of BHB only, HMB only, and a combination of BHB and HMB, showing that improvement in the lean-to-fat mass ratio is expected to be greater with the combination treatment by more than just the sum of the BHB only and HMB only treatments.

FIG. 3 illustrates expected improvement in the lean-to-fat mass ratio resulting from treatments of HMB only (HMB), BHB only (BHB), and a combination of the same amounts of HMB and BHB (HMB+BHB). For a given lean-to-fat mass ratio goal, the expected results show that the combined treatment promotes increases in the lean-to-fat ratio by more than the sum of the BHB only and HMB only treatments. That is, the combined treatment leads to more rapid results and to better overall results for a given time period. Although BHB is shown here as the ketone body component, other ketone body components described herein may additionally or alternatively be utilized with similarly beneficial results expected.

Figure 4A:
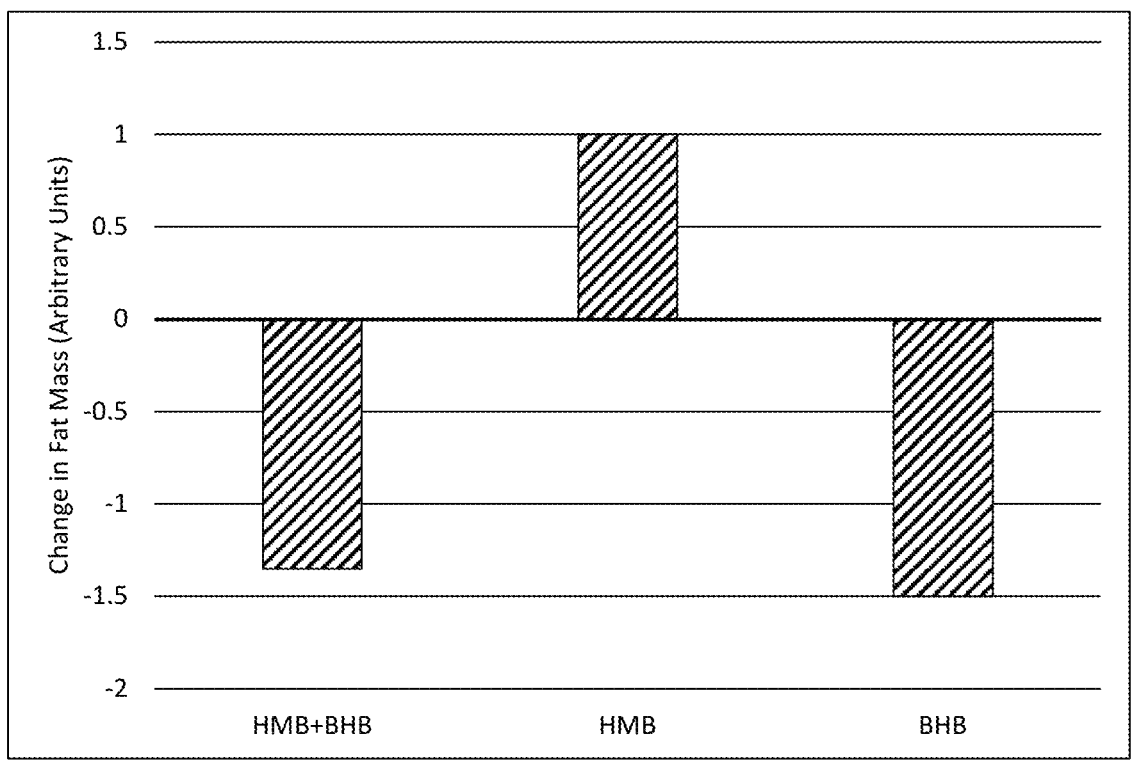
FIG. 4A illustrates expected changes in fat mass from different respective treatments of BHB only, HMB only, and a combination of BHB and HMB, showing better fat loss with the combination treatment.

FIG. 4A illustrates expected change in fat mass over a set period of time (e.g., 1-3 months) for subjects following a training regimen and given different treatments of HMB only (HMB), BHB only (BHB), and a combination of the same amounts of HMB and BHB (HMB+BHB). The expected results show that the HMB treatment is not expected to provide fat loss to any significant degree by itself, and may even be associated with fat gain due to its anabolic properties, whereas the BHB treatment is expected to provide effective levels of fat loss. The combination HMB+BHB treatment is also expected to provide fat loss. Although the amount of fat loss with the HMB+BHB treatment may be somewhat less than with the BHB only treatment, the overall effects on body composition from the HMB+BHB treatment are expected to be enhanced relative to the other treatments, as explained below with reference to FIG. 4C. Although BHB is shown here as the ketone body component, other ketone body components described herein may additionally or alternatively be utilized with similarly beneficial results expected.

Figure 4B:
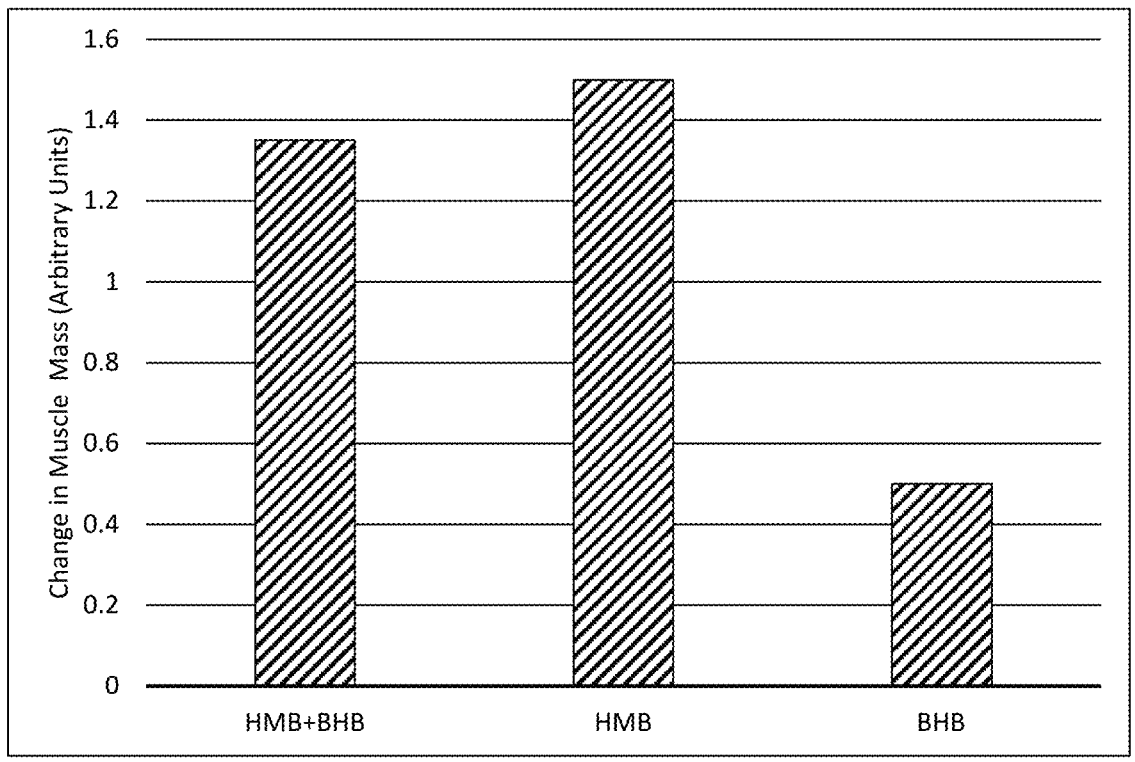
FIG. 4B illustrates expected changes in muscle mass from different respective treatments of BHB only, HMB only, and a combination of BHB and HMB, showing greater gains in muscle mass with the combination treatment.

FIG. 4B illustrates expected change in muscle mass over a set period of time (e.g., 1-3 months) for subjects following a training regimen and given different treatments of HMB only (HMB), BHB only (BHB), and a combination of the same amounts of HMB and BHB (HMB+BHB). The expected results show that the BHB treatment is not expected to provide significant improvements to muscle mass alone, whereas the HMB treatment is expected to allow for somewhat greater increases in muscle mass. The combination HMB+BHB treatment is also expected to promote muscle growth. Although the amount of muscle gain with the HMB+BHB treatment may be somewhat less than with the HMB only treatment, the overall effects on body composition from the HMB+BHB treatment are expected to be enhanced relative to the other treatments, as explained below with reference to FIG. 4C. For example, subjects given the HMB+BHB treatment may be better able to translate results from a weightlifting program into observed muscle gains, even though they are involved in a fasting regimen that leads to fat loss over the same time period. Although BHB is shown here as the ketone body component, other ketone body components described herein may additionally or alternatively be utilized with similarly beneficial results expected.

Figure 4C:
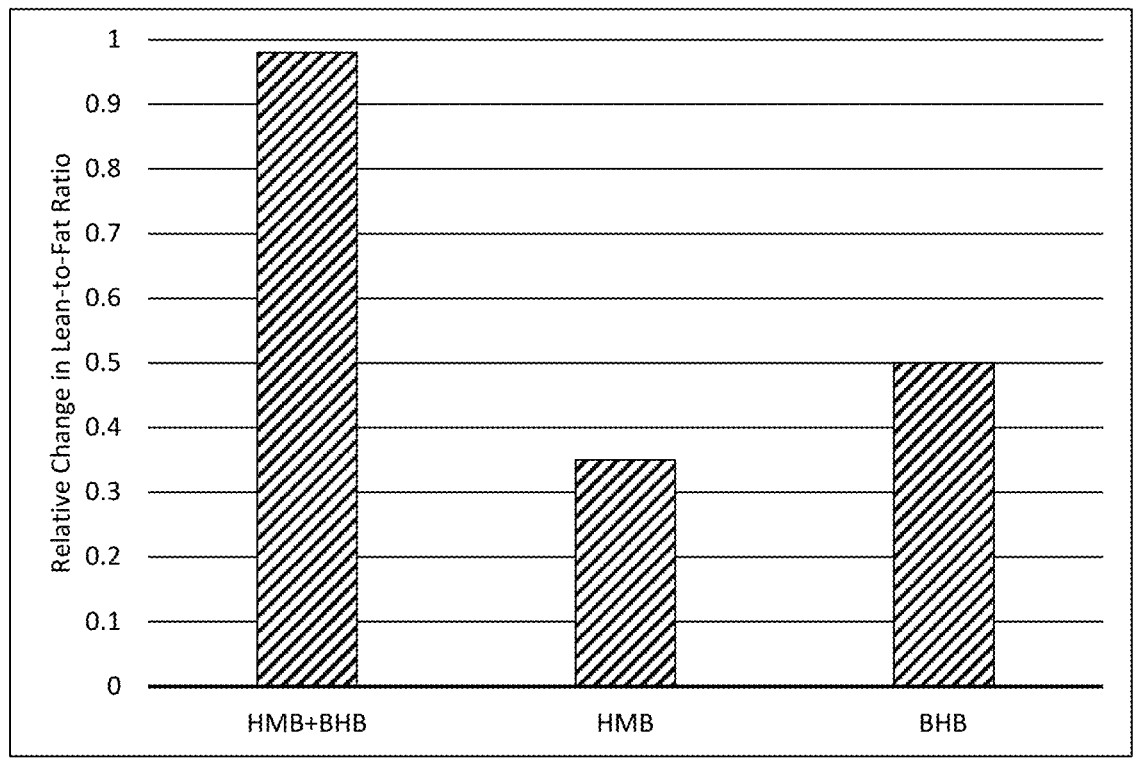
FIG. 4C illustrates the combined effect of the changes in fat mass shown in FIG. 4A and the changes in muscle mass shown in FIG. 4B, showing that the resulting change in the lean-to-fat mass ratio is greater with the combination treatment by more than just the sum of the BHB only and HMB only treatments.

FIG. 4C illustrates the combined effect of the changes in fat mass shown in FIG. 4A and the changes in muscle mass shown in FIG. 4B, showing that the resulting change in the overall lean-to-fat mass ratio is greater with the combination treatment by more than just the sum of the BHB only and HMB only treatments. In other words, the effects of the HMB and BHB in the combined treatment provide synergistic effects on the lean-to-fat mass ratio that are greater than would be expected through additive effects of the components used independently. Although BHB is shown here as the ketone body component, other ketone body components described herein may additionally or alternatively be utilized with similarly beneficial results expected.

FIGS. 5A through 5D illustrate a fasting window (e.g., a typical window for an intermittent fasting period of about 16-20 hours) and compares expected effects on fat and muscle over time for no treatment (control), a BHB only treatment (BHB Treatment), an HMB only treatment (HMB Treatment), and a combination of HMB and BHB treatment (HMB+BHB Treatment). The shaded area between the fat and muscle lines represents the relative change in these two types of mass, and a greater shaded area thus represents greater improvements in the lean-to-fat mass ratio. Although BHB is shown here as the ketone body component, other ketone body components described herein may additionally or alternatively be utilized with similarly beneficial results expected.

Figure 5A:
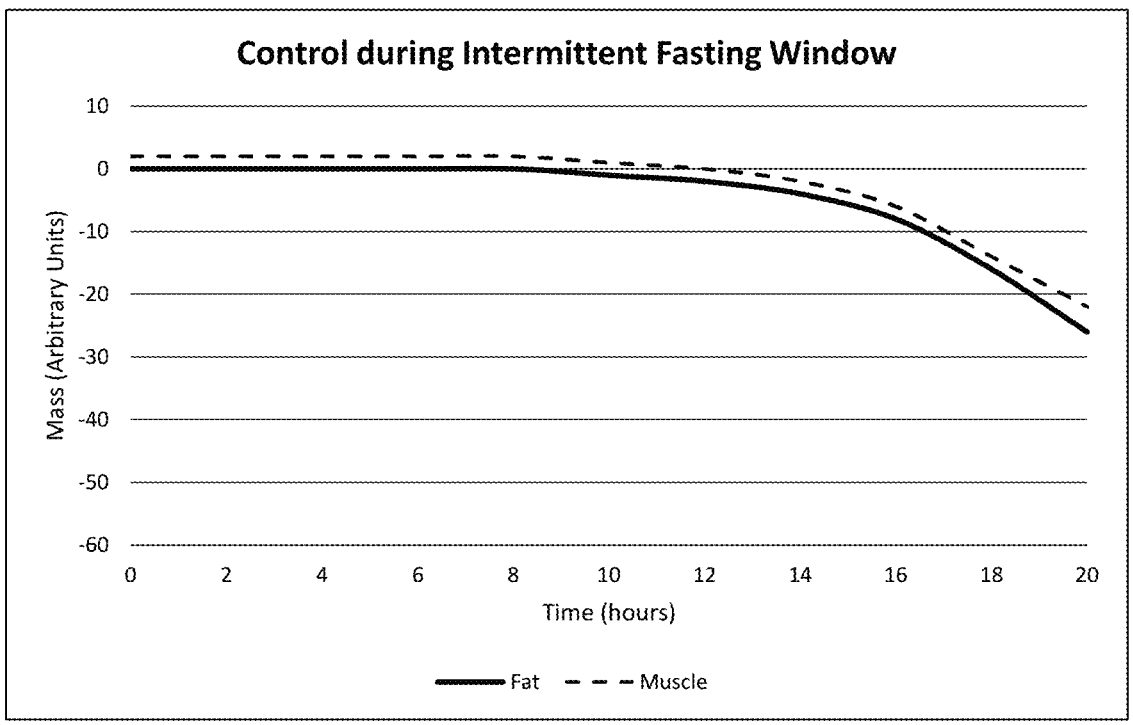
FIGS. 5A through 5D illustrate a fasting window and compare expected fat and muscle effects over time for no treatment, a BHB only treatment, an HMB only treatment, and a combination of BHB and HMB treatment.
Figure 5B:
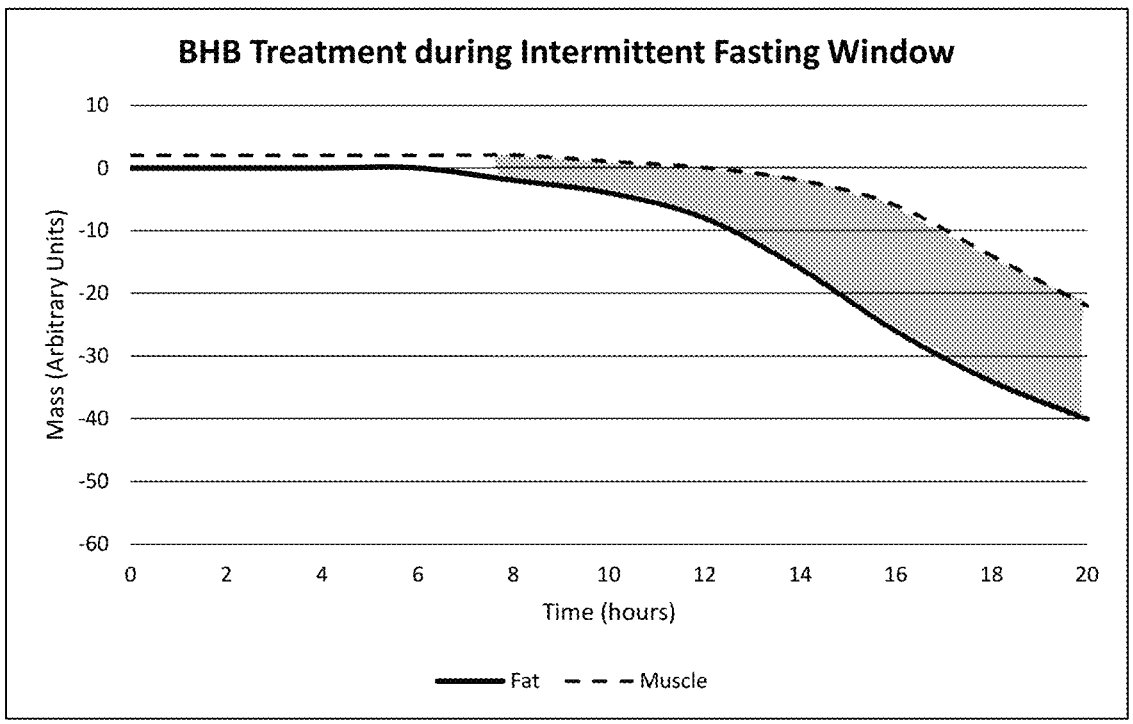
Figure 5C:
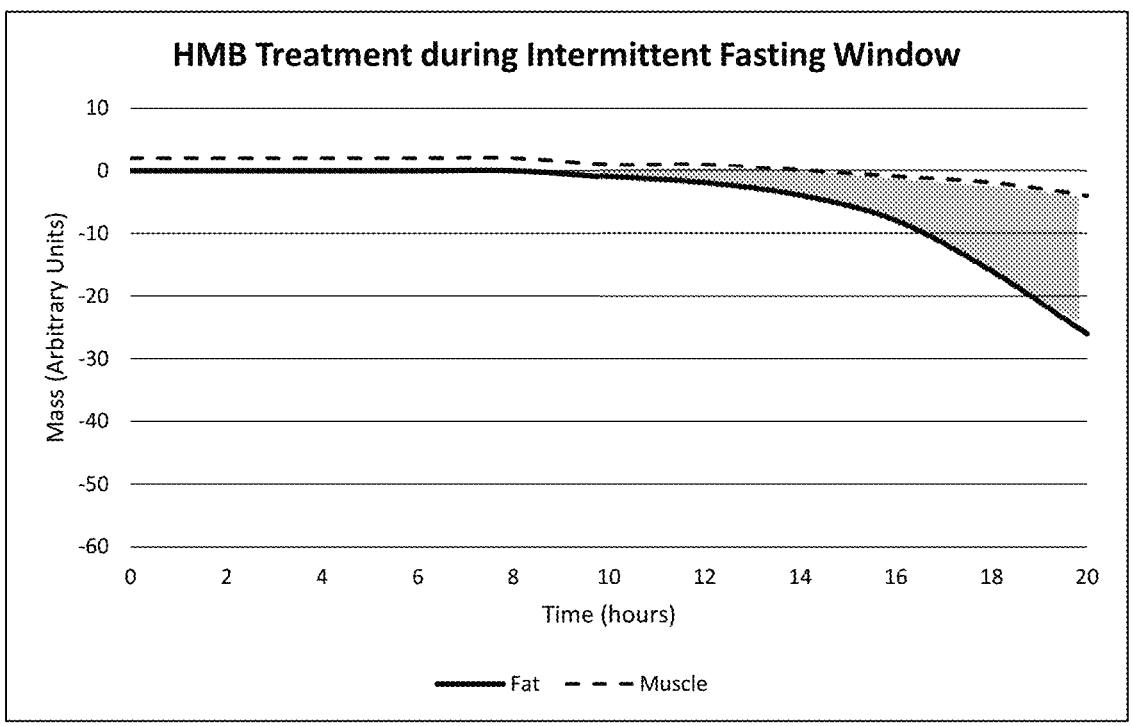

As shown in FIG. 5A, fat loss may slowly begin at around the 12- to 14-hour mark into the fast and then becomes more pronounced as the fast continues. However, muscle loss may also begin at about the same time and likewise may become more pronounced as the fast progresses. With the BHB Treatment shown in FIG. 5B, fat loss may begin somewhat sooner and progress somewhat more rapidly, leading to greater overall fat loss over the time period as compared to the control. However, the muscle loss will be substantially the same as with the control. With the HMB Treatment shown in FIG. 5C, muscle loss will be reduced as compared to the control, but fat loss will be substantially the same as with the control.

Figure 5D:
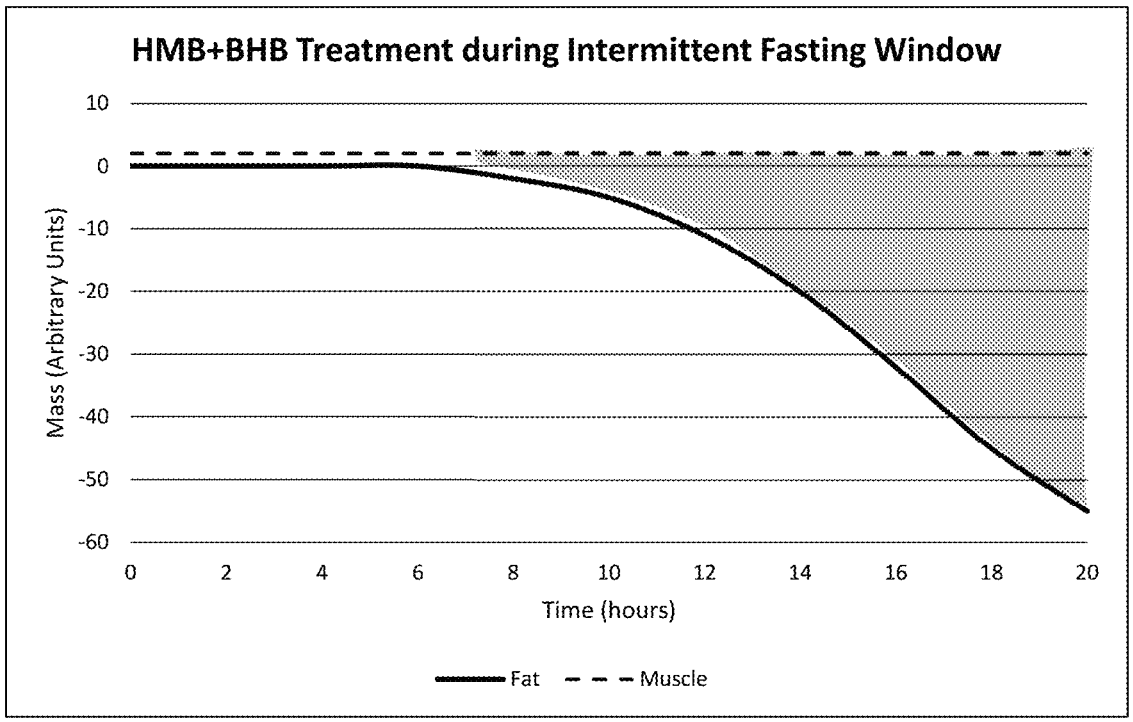

With the HMB+BHB Treatment shown in FIG. 5D, the synergistically enhanced effects of the two components are expected to both prevent muscle loss and enhance fat loss, whereas the other treatments are not expected to provide both of these effects simultaneously. Moreover, because of the synergies involved between the two components, the HMB+BHB Treatment is expected to maintain muscle mass to a greater degree than the HMB Treatment, and to enhance fat loss to a greater degree than the BHB Treatment. As compared to the control treatment as a baseline, the fat loss effects and muscle maintenance effects of an HMB+BHB Treatment are believed to be greater than what would be predicted based on simply adding the improvements over the control when each component is used independently.

B. Neuroprotection/Memory

Neuroprotection and enhanced memory are associated with exogenous ketone body supplementation as well as with ketosis, which may be induced by the use of exogenous ketone bodies. When the brain switches from using glucose as its primary fuel source to using ketone bodies as its primary fuel source, the resulting metabolic state provides additional protection against neurodegenerative conditions such as epilepsy and possibly Alzheimer's and Parkinson's diseases (see, e.g., Gasior et al. "Neuroprotective and disease-modifying effects of the ketogenic diet" Behav. Pharmacol. 2006 September; 17 (5-6): 431-39).

Ketone bodies, in particular BHB, are potent free radical scavengers and provide direct antioxidant effects. Because the brain actively utilizes ketone bodies when they are available, the relatively high concentration of ketone bodies in the brain following supplementation therefore provides an effective antioxidant neuroprotective function. Further, BHB molecular signaling provides indirect antioxidant effects via endogenous enzyme upregulation. For example, BHB molecular signaling may be associated with Class I and II histone deacetylase (HDAC) inhibition, which is related to mitigation of neurodegenerative diseases (e.g., Alzheimer's disease), and has positive effects on memory, among other effects. BHB may also increase gene expression of various endogenous defense proteins such as FOXO3 (tumor inhibitor), reactive oxygen species (ROS) scavengers such as catalase and SOD2, and toxic metal scavengers such as metallothionein. BHB may also act as an agonist of the $HCA_2$ protein. As with high-dose niacin supplementation, this is associated with anti-inflammatory effects in a variety of tissues including the brain.

It is expected that the neuroprotective and/or memory enhancing effects of ketone bodies and HMB are synergistically enhanced as a result of their combined administration. The ketone body component of the composition is expected to provide these effects and also to aid in inducing and sustaining ketosis in the subject, which will lead to neuroprotective and/or memory enhancing effects. Further, the HMB component is expected to further provide neuroprotection and/or memory enhancement through its modulation of protein utilization. It is expected that the resulting neuroprotective and/or memory effects will be greater than that possible with either component alone and/or will be greater than the sum of the effects of each component when used independently. The beneficial neuroprotective effects of a KB-HMB composition may be particularly useful in treating and/or managing Alzheimer's disease, Parkinson's disease, and epilepsy, for example.

C. Anti-Aging/Longevity

The ability of HMB to promote muscle building and/or reduce muscle wasting can promote longevity in the user. Following a strict ketogenic diet can sometimes have the unwanted effect of depleting not only fat but muscle tissue as well. In addition, muscle formation diminishes with increased age. Combining BHB and HMB has been found to synergistically increase energy while also reducing or eliminating muscle wasting and/or promoting muscle formation.

Ketone body supplementation may also be associated with longevity promoting effects. As discussed above, ketone body supplementation can positively influence mitochondrial health, including raising the number of mitochondria and raising the concentration of antioxidants in the mitochondria to prevent reactive oxygen species (ROS) damage to the mitochondria. BHB may also stimulate chaperone-mediated autophagy of certain proteins marked by BHB oxidative modification (see Finn et al. "Ketone bodies stimulate chaperone-mediated autophagy" J. Biol. Chem. Jul. 8, 2005; 280(27): 25864-70).

The longevity promoting effects of HMB and exogenous ketone body supplementation are expected to be synergistically enhanced as a result of their combined administration. It is expected that the longevity effects of a KB-HMB composition will be greater than that possible with either component alone and/or will be greater than the sum of the effects of each component when used independently. Longevity is of course a multifaceted issue, and the longevity enhancing effects of KB-HMB supplementation may be further promoted by other beneficial effects described herein, such as neuroprotection, antioxidant effects, anti-inflammatory effects, cardiovascular health effects, and promotion of fat loss.

D. Anti-Inflammation/Analgesic

Exogenous ketone body supplementation may reduce inflammation, and in addition may induce ketosis and thereby further act to reduce inflammation. When under ketone body supplementation and/or when in ketosis, less insulin is produced, there is a reduction in inflammation markers, and there is a reduction in the generation of free radicals, which are known to contribute to inflammation. Ketone bodies also increase levels of adenosine, which is known to reduce inflammation and reduce pain. BHB also activates the AMPK pathway, which decreases inflammation and pain, and also inhibits the COX-2 enzyme in a manner somewhat similar to conventional non-steroidal anti-inflammatory drugs. BHB also inhibits the NLRP3 inflammasome, which is the pathway involved in initiating the inflammatory response.

BHB molecular signaling can further provide beneficial anti-inflammatory activity. For example, BHB molecular signaling may be associated with Class I and II histone deacetylase (HDAC) inhibition, which is related to inflammation control among other effects. BHB may also function to reduce expression of NALP3, which is a major component of the inflammasome. BHB may also increase gene expression of various endogenous defense proteins such as FOXO3 (tumor inhibitor), ROS scavengers such as catalase and SOD2, and toxic metal scavengers such as metallothionein. BHB may also act as an agonist of the $HCA_2$ protein. As with high-dose niacin supplementation, this is associated with anti-inflammatory effects in a variety of tissues including the brain, gastrointestinal tract, skin, and vascular tissue.

Although the anti-inflammatory properties discussed above may themselves lead to reductions in pain, the combined administration of HMB in combination with the ketone bodies is expected to further reduce excess inflammation caused by protein tissue breakdown resulting from following a strict ketogenic diet. Although some baseline levels of inflammation are expected, given that some amount of inflammation is associated with general immunological function, tissue healing, and muscle repair, excess levels of inflammation beyond such healthy baselines are expected to be reduced. Thus, administration of the KB-HMB composition permits the user to be in a catanabolic state, with an appropriate amount of muscle breakdown and inflammation for both catabolism and building to occur, together with an appropriate quantity of energy for quick repair and leaning up.

It is expected that the anti-inflammatory effects of HMB and ketone bodies are synergistically enhanced as a result of their combined administration. The ketone body component of the composition is expected to lead to reductions in inflammation by way of reduced reactive oxygen species and increased levels of adenosine, for example, and these effects may be further enhanced as a result of the ketone bodies inducing or sustain ketosis in the subject. The HMB component is meanwhile expected to further reduce excessive inflammation through its modulation of proteolytic activity. It is expected that the resulting anti-inflammatory and analgesic effects will be greater than that possible with either component alone and/or will be greater than the sum of the effects of each component when used independently.

E. Anxiolytic/Anti-Depressant

HMB has been found to provide antidepressant activity. As described in EP 2745708A1, "Antidepressant effect of β-hydroxy-β-methylbutyrate", HMB supplementation can treat or prevent depression through modulation of mTOR signaling, including possibly through activation of mTOR signaling in neuronal cells.

BHB molecular signaling can further provide beneficial anxiolytic/anti-depressant activity. For example, BHB molecular signaling may be associated with Class I and II histone deacetylase (HDAC) inhibition, which has positive effects on mood, among other effects. BHB may also increase synthesis of gamma-Aminobutyric acid (GABA) in the brain, thereby promoting a calming, anxiolytic effect. Ketone bodies such as BHB and acetoacetate may function synergistically with HMB to modulate GABA and/or GABA receptor activity.

Many individuals report a reduction in depressive symptoms as a result of a ketogenic diet, most likely due to general increases in physiological health. However, some individuals may experience an increase in symptoms of depression during ketosis because of difficulties in producing the neurotransmitter serotonin. Low serotonin levels are associated with depression and anxiety. Serotonin is derived from the essential amino acid tryptophan, which must be consumed in the diet. Tryptophan has a better likelihood of passing the blood-brain barrier, where it can be converted to serotonin, when it is at a higher blood concentration relative to other proteins and amino acids. When insulin is released, it functions to "pull" these other proteins and amino acids into muscles, leaving a higher proportion of tryptophan remaining in the blood to cross the blood-brain barrier.

With a low-carb ketogenic diet, however, lower carbohydrate intake means less insulin is released. Thus, although a ketogenic diet includes an abundance of tryptophan, less tryptophan will cross the blood-brain barrier to be available for serotonin production because it must compete with other protein components in the blood. The beneficial anxiolytic and anti-depressant effects of HMB can therefore complement the supplementation of exogenous ketone bodies by counteracting the potential negative effects related to low serotonin production.

F. Cardiovascular Health

Nissen et al., "β-Hydroxy-β-Methylbutyrate (HMB) Supplementation in Humans Is Safe and May Decrease Cardiovascular Risk Factors," *The Journal of Nutrition*, Volume 130, Issue 8, August 2000, Pages 1937-194, teaches that HMB can improve cardiovascular health, including by decreasing total cholesterol, LDL cholesterol, and systolic blood pressure.

Exogenous ketone bodies may also aid in lowering blood pressure and/or improving cardiovascular health, and additionally may induce a sustained state of ketosis to further promote these effects. Ketosis can reduce the retention of sodium ions associated with high blood pressure. The lowered insulin release associated with ketosis may also correspond to reduced blood pressure.

BHB molecular signaling can further provide beneficial cardiovascular effects. For example, BHB may act as an agonist of the $HCA_2$ protein. As with high-dose niacin supplementation, this is associated with anti-inflammatory effects in a variety of tissues including vascular tissue. It is also associated with increasing levels of HDL cholesterol, reducing atherogenic activity, and promoting vasodilation.

It is expected that the beneficial cardiovascular effects of HMB and ketone bodies are synergistically enhanced as a result of their combined administration. The ketone body component of the composition is expected to lead to reductions in blood pressure and additionally may aid in inducing and sustaining ketosis in the subject to further promote these effects. The HMB component is meanwhile also expected to promote cardiovascular health through reductions in total cholesterol, LDL cholesterol, and systolic blood pressure. It is expected that the cardiovascular effects will be greater than that possible with either component alone and/or will be greater than the sum of the effects of each component independently.

IV. Dosage Forms and Administration

Compositions described herein may be provided in various forms, such as one-part or multi-part compositions configured for administration by one or more of ingestion, intragastric, injection, topical application, inhalation, oral mucosal administration, rectal administration, vaginal administration, or parenteral administration.

Non-limiting examples of the foregoing administration routes include, but are not limited to, ingestible compositions, suppositories (anal or vaginal), transdermal patch, sublingual compositions, subdermal modalities, solid, powder, liquid, gel, tablet, capsule, other dietetically or pharmaceutically acceptable form, vaporizable cartridge, nebulizing liquid, smokable bolus, syringe for intravenous injection, nasal spray or vapor, inhalable pulmonary composition, enema, douche, injectable bolus, subdermal implant (e.g., pellet or stick), and the like.

Inhalation can be performed using a heat vaporizer (e.g., vape stick, mod box, e-cigarette, or vape cartridge), smoking a bolus (e.g., using a pipe, water pipe, bong, rolling papers, glass pipe, chillum, one-hitter, hookah, apple pipe, avocado pipe, gas mask, snorkel gear), or a nebulizer.

Edibles include drinks, soda, energy shots, sparkling water, beer, wine, spirits, hard seltzer, coconut water, fruit juices, chocolate, fruit chews, oral drops, coconut oil, butter, water, milk, cookies, cake, ice cream, gummy bears, pizza crust, brownies, pastries, yogurt, frozen yogurt, chewable vitamins, candy, protein powder, supplements, supplement powders, consumable powders, coffee, tea, and the like.

Oral/concentrates/extractions include chewing gum, tinctures, oils, sublingual sprays, pills, capsules, quick-dissolve tablets, troches, nasal sprays, eyedrops, dabs, shatter, and rosin.

Topicals include lotions, creams, salves, balms, transdermal patches, gels, shampoo, conditioner, deodorant, lip balm, lipstick, and makeup.

Solid or powder compositions may include one or more additional components configured to lower the hygroscopicity of the composition. For example, various anticaking agents, flow agents, and/or moisture absorbers, in types and amounts that are safe for consumption, may be included. Such additional components may include one or more of an aluminosilicate, ferrocyanide, carbonate or bicarbonate salt, silicate (e.g., sodium or calcium silicate), phosphate salt (e.g., tricalcium phosphate), talcum, powdered cellulose, and the like.

In alternative embodiments, the KB-HMB composition may be provided as a liquid, such as in the form of a shot or mouth spray for fast delivery and absorption, or as a gel. Liquid or gel forms may include one or more carriers, such as water, ethanol, glycerin, propylene glycol, 1,3-propandiol, and the like, into which the components are dissolved or dispersed. The composition may include flavoring agents that help mask the somewhat poor taste of BHB compounds. These flavoring agents may include essential oils, such as peppermint, natural and artificial sweeteners, and other flavorants known in the art.

The KB-HMB composition may include one or more supplements known in the art, such as vitamins, minerals, and caffeine or other stimulants. For example, caffeine may be included in an amount of about 10 mg to about 250 mg, or about 25 mg to about 170 mg, or about 40 mg to about 120 mg.

The KB-HMB compositions described herein may be provided within a dosage regimen effective in inducing and sustaining ketosis and/or providing other benefits described herein. For example, the mass of exogenous ketone bodies in a daily dose (for an average adult of about 175 lbs.) may range from about 0.5 gram to about 50 grams, or about 1 gram to about 40 grams, or about 2 grams to about 30 grams, or about 3 grams to about 25 grams, or about 4 grams to about 20 grams, and may be provided using one or more unit doses. The mass of the HMB component in a daily dose (for an average adult of about 175 lbs.) may range from about 0.25 gram to about 10 grams, or about 0.5 gram to about 5 grams, or about 1 gram to about 3 grams. As needed, dosages may be adjusted (e.g., linearly) based on weight of the subject. The HMB component and the ketone body component may be mixed/combined, though some methods may provide the components separately. The daily dose(s) may be taken as a single daily dose or as multiple doses (e.g., 2, 3, or 4 times daily).

In some embodiments, the composition includes a ratio of the ketone body component to the HMB component in a range of about 5:1 to about 1:5, though it is more preferable that the amount of the ketone body component is at least as much and may be somewhat greater than HMB. For example, a more preferable ratio of the ketone body component to the HMB may range from about 5:1 to about 1:1, or from about 4:1 to about 1.5:1. Example weight ratios of ketone body component(s) to HMB component(s) include 1:5, 1:4, 1:3, 1:2, 1:1.5, 1:1, 1.5:1, 2:1, 3:1, 4:1, and 5:1, and any range with any of the foregoing as endpoints. Preferable weight ratios of ketone body component(s) to HMB component(s) are 1:1, 1.25:1, 1.5:1, 1.75:1, 2:1, 2.5:1 3:1, 3.5:1, 4:1, 4.5:1, and 5:1.

In a preferred embodiment, a KB-HMB composition is administered in one or more unit doses per day via oral administration of the composition in a solid, powdered form or liquid, such as in a powdered mixture (e.g., powder filled gelatin capsules), hard-pressed tablets, or other oral administration route known to those skilled in the art.

In some embodiments, multiple doses of the composition are administered. The frequency of administration of the composition can vary depending on any of a variety of factors, such as timing of treatment from previous treatments, objectives of the treatment, and the like. The duration of administration of the composition (e.g., the period of time over which the agent is administered), can vary depending on any of a variety of factors, including subject response, desired effect of treatment, etcetera.

The amount of the composition to be administered can vary according to factors such as the degree of susceptibility of the individual, the age, sex, and weight of the individual, idiosyncratic responses of the individual, and the like. The "therapeutically effective amount" is that amount necessary to promote a therapeutically effective result in vivo. In accordance with the present disclosure, a suitable single dose size is a dose that is capable of preventing or alleviating (reducing or eliminating) a symptom in a patient when administered one or more times over a suitable time period (e.g., a daily dose).

The amount of composition administered will depend on potency, absorption, distribution, metabolism, and excretion rates of the composition components, the method of administration, and the particular disorder being treated, as well as other factors known to those of skill in the art. The dose should be sufficient to affect a desirable response, such as a therapeutic or prophylactic response against a particular disorder or condition, taking into account the severity of the condition to be alleviated. The compounds may be administered once over a given time period (e.g., once per day), or may be divided and administered over intervals of time. It is to be understood that administration may be adjusted according to individual need and professional judgment of a person administrating or supervising the administration of the compositions.

VII. EXAMPLES

The following is a description of exemplary KB-HMB compositions useful for increasing lean-to-fat mass ratio in a subject.

Example 1

A KB-HMB composition is prepared by mixing a ketone body component comprising one or more of sodium beta-hydroxybutyrate, potassium beta-hydroxybutyrate, magnesium beta-hydroxybutyrate, or calcium beta-hydroxybutyrate with an HMB component comprising one or more of sodium beta-hydroxy-beta-methylbutyrate, potassium beta-hydroxy-beta-methylbutyrate, magnesium beta-hydroxy-beta-methylbutyrate, or calcium beta-hydroxy-beta-methylbutyrate. The weight ratio of ketone body component to HMB component is 2:1. The KB-HMB composition is in a form that is readily administered, such as in powder form as a dietary supplement mixed with food or drink, in the form of one or more capsules or tablets, or in liquid form such as a mouth spray, liquid shot, or beverage.

Example 2

A KB-HMB composition is prepared by mixing a ketone body component comprising one or more of sodium beta-hydroxybutyrate, potassium beta-hydroxybutyrate, magnesium beta-hydroxybutyrate, or calcium beta-hydroxybutyrate with an HMB component comprising one or more of sodium beta-hydroxy-beta-methylbutyrate, potassium beta-hydroxy-beta-methylbutyrate, magnesium beta-hydroxy-beta-methylbutyrate, or calcium beta-hydroxy-beta-methylbutyrate. The weight ratio of ketone body component to HMB component is 3:1. The KB-HMB composition is in a form that is readily administered, such as in powder form as a dietary supplement mixed with food or drink, in the form of one or more capsules or tablets, or in liquid form such as a mouth spray, liquid shot, or beverage.

Example 3

A KB-HMB composition is prepared by mixing a ketone body component comprising one or more of sodium beta-hydroxybutyrate, potassium beta-hydroxybutyrate, magnesium beta-hydroxybutyrate, or calcium beta-hydroxybutyrate with an HMB component comprising one or more of sodium beta-hydroxy-beta-methylbutyrate, potassium beta-hydroxy-beta-methylbutyrate, magnesium beta-hydroxy-beta-methylbutyrate, or calcium beta-hydroxy-beta-methylbutyrate. The weight ratio of ketone body component to HMB component is 4:1. The KB-HMB composition is in a form that is readily administered, such as in powder form as a dietary supplement mixed with food or drink, in the form of one or more capsules or tablets, or in liquid form such as a mouth spray, liquid shot, or beverage.

Example 4

Any of the foregoing Examples is modified by substituting a portion of the beta-hydroxybutyrate salts(s) with beta-hydroxybutyric acid.

Example 5

Any of the foregoing Examples is modified by including one or more esters of beta-hydroxybutyrate and/or acetoacetate.

Example 6

Any of the foregoing Examples is modified by substituting part or all of the beta-hydroxybutyrate salt(s) with one or more of sodium acetoacetate, potassium acetoacetate, magnesium acetoacetate, or calcium acetoacetate.

Example 7

Example 6 is modified by substituting a portion of the acetoacetate salt(s) with acetoacetic acid.

Example 8

Any of the foregoing Examples is modified by being in a dosage form that provides from about 0.5 gram to about 50 grams, or about 1 gram to about 40 grams, or about 2 grams to about 30 grams, or about 3 grams to about 25 grams, or about 4 grams to about 20 grams, of the ketone body component.

Example 9

Any of the foregoing Examples is modified by being in a dosage form that provides from about 0.25 gram to about 10 grams, or about 0.5 gram to about 5 grams, or about 1 gram to about 3 grams, of the HMB component.

Example 10

Any of the foregoing Examples is modified by including one or more supplements, including one or more of vitamin(s), mineral(s), herb(s), or stimulant(s).

Example 11

Any of the foregoing Examples is modified to include a liquid carrier selected from water, ethanol, glycerin, propylene glycol, and 1,3-propandiol.

Example 12

Any of the foregoing Examples is modified to include a ketone body precursor selected from 1,3-butanediol, fatty acids, and/or esters of fatty acids, such as one or more medium chain fatty acids or one or more medium chain triglycerides (MCT).

Example 13

Any of the foregoing Examples is modified to include a short-chain fatty acid or ester thereof.

Example 14

Any of the foregoing Examples is modified by combining the mixed salt composition with one or more fat burner supplements such as green tea, green tea extract (e.g., a composition including one or more isolated green tea catechins such as epigallocatechin gallate (EGCG)), green coffee extract, conjugated linoleic acid (CLA), tetradecyl thioacetic acid (TTA), *Coleus forskohlii* (i.e., forskolin), yohimbine, rauwolscine, capsaicin, raspberry ketones (e.g., 4-(4-hydroxyphenyl) butan-2-one, p-hydroxybenzyl acetone), ephedrine, synephrine (e.g., bitter orange extract), octopamine, 1,3-dimethylamylamine, higenamine, fucoxanthin, acetylcholine modulators and/or adenosine receptor antagonists (e.g., caffeine), nicotine, coca leaf derivative, ursolic acid, clenbuterol, noradrenaline reuptake inhibitors (e.g., hordenine, atomoxetine), 7-oxodehydroepiandrosterone (i.e., 7-keto DHEA), thyroid hormones (e.g., triiodothyronine), and combinations thereof. The resulting composition is expected to provide greater lipolysis and/or fat oxidation effects.

Example 15

Any of the foregoing Examples is modified by combining the mixed salt composition with one or more nootropic supplements such as tyrosine, L-DOPA (i.e., L-3,4-dihydroxyphenylalanine), tryptophan, and 5-hydroxytryptophan (5-HTP), racetams such as such as piracetam, oxiracetam, and aniracetam, L-theanine, D-serine, phosphatidylserine, tolcapone, uridine, vinpocetine, norepinephrine reuptake inhibitors such as hordenine and atomoxetine, *Panax ginseng*, *Ginkgo biloba*, *Rhodiola rosea*, *Polygala tenuifolia*, *Muira puama*, *Eschscholzia californica*, *Convolvulus pluricaulis*, *Centella asiatica*, *Evolvulus alsinoides*, *Bacopa monnieri*, *Epimedium* herbs, Ashwagandha herbs, cyclic adenosine monophosphate (cAMP) modulators such as forskolin, stimulants such as nicotine, caffeine, and amphetamines, cholinergic compounds and/or acetylcholine modulators such as huperzine-A, dimethylaminoethanol, choline, and alpha-glycerophosphocholine, and combinations thereof. The resulting combined supplement is expected to provide greater cognition, alertness, and/or mood effects.

Example 16

Any of the foregoing Examples is modified by including pharmaceutically or dietetically acceptable carrier.

Example 17

Any of the foregoing Examples is modified by being in a dosage form configured for administering by one or more of ingestion, intragastric, injection, topical, inhalation, oral mucosal, rectal, vaginal, or parenteral.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A composition comprising:
an exogenous ketone body component selected from the group consisting of beta-hydroxybutyrate (BHB) salts, BHB esters, beta-hydroxybutyric acid, and combinations thereof; and
exogenous hydroxymethyl butyrate (HMB),
wherein the composition includes a ratio of exogenous ketone body component to exogenous HMB from about 4.5:1 to about 2.5:1 so as to be effective to increase lean mass to fat mass ratio in a mammal.

2. The composition of claim 1, wherein the exogenous ketone body component includes an exogenous BHB salt or ester.

3. The composition of claim 1, further comprising one or more of 1,3-butanediol, acetoacetate salt, acetoacetate ester, acetoacetic acid, or an exogenous fatty acid or an ester thereof.

4. The composition of claim 3, wherein the exogenous fatty acid or ester thereof is a medium chain fatty acid or ester thereof, or a short chain fatty acid or ester thereof.

5. The composition of claim 1, wherein the composition comprises an ester formed between a ketone body and HMB.

6. The composition of claim 1, wherein the composition comprises a mixed anion salt comprising a multivalent cation, an exogenous ketone body anion, and an exogenous HMB anion.

7. The composition of claim 1, wherein the composition comprises a mixed salt comprising a plurality of exogenous cations selected from the group consisting of lithium ions, sodium ions, potassium ions, magnesium ions, calcium ions, and amino acid cations, exogenous ketone body anions, and exogenous HMB anions.

8. The composition of claim 1, wherein the composition is provided in solid or powder form.

9. The composition of claim 1, wherein the composition is provided in liquid form.

10. The composition of claim 1, wherein the composition is in a dosage form that provides from about 0.5 gram to about 50 grams, or about 1 gram to about 40 grams, or about 2 grams to about 30 grams, or about 3 grams to about 25 grams, or about 4 grams to about 20 grams, of the exogenous ketone body component.

11. The composition of claim 1, wherein the composition is in a dosage form that provides about 0.25 gram to about 10 grams, or about 0.5 grams to about 5 grams, or about 1 gram to about 3 grams, of the exogenous HMB.

12. The composition of claim 1, further comprising a pharmaceutically or dietetically acceptable carrier.

13. A mixed salt composition comprising:
   a plurality of exogenous cations selected from alkali metal cations, alkaline earth metal cations, transition metal cations, and amino acid cations; and
   a plurality of anions comprising exogenous ketone body anions and exogenous HMB anions,
   wherein at least a portion of the mixed salt composition comprises a multivalent cation forming a salt with at least one exogenous ketone body anion and at least one exogenous HMB anion,
   wherein the mixed salt composition includes a ratio of exogenous ketone body anions to exogenous HMB anions from about 4.5:1 to about 2.5:1 so as to be effective to increase lean mass to fat mass ratio in a mammal.

14. A method for administering exogenous ketone bodies and exogenous HMB to a mammal to increase lean mass to fat mass ratio in the mammal, comprising:
   administering about 0.5 gram to about 50 grams of an exogenous ketone body component selected from beta-hydroxybutyrate (BHB) salts, BHB esters, beta-hydroxybutyric acid, and combinations thereof; and
   administering about 0.25 gram to about 10 grams of exogenous HMB,
   wherein a ratio of the exogenous ketone body component to the exogenous HMB is in a range of about 4.5:1 to about 2.5:1 so as to be effective to increase lean mass to fat mass ratio in the mammal.

15. The method of claim 14, wherein administering comprises administering multiple doses per day.

16. The method of claim 14, wherein the method is effective to provide one or more of homeostasis promotion, neuroprotection, memory enhancement, an anxiolytic effect, an anti-depressant effect, an anti-inflammatory effect, an analgesic effect, an antioxidant effect, blood pressure modulation, heart rate modulation, or a longevity promoting effect.

17. The method of claim 14, wherein the ketone body component is effective to increase the pharmacokinetic utilization of the HMB relative to pharmacokinetic utilization of the HMB in the absence of the ketone body component.

18. The method of claim 14, wherein the method is effective to accelerate the production of endogenous ketones in the mammal as a result of increased availability of ketone body precursors.

19. The method of claim 14, wherein administering comprises one or more of ingestion, intragastric, injection, topical, inhalation, oral mucosal, rectal, vaginal, or parenteral.

20. A composition comprising:
   an exogenous ketone body component selected from the group consisting of beta-hydroxybutyrate (BHB) salts, BHB esters, beta-hydroxybutyric acid, and combinations thereof; and
   exogenous hydroxymethyl butyrate (HMB),
   wherein the composition is in a dosage form that provides from about 0.5 gram to about 50 grams of the exogenous ketone body component and about 0.25 gram to about 10 grams of the exogenous HMB,
   wherein a ratio of the exogenous ketone body component to the exogenous HMB is in a range of about 4.5:1 to about 2.5:1 so that the composition is effective to increase lean mass to fat mass ratio in a mammal.

* * * * *